(12) United States Patent
Austera et al.

(10) Patent No.: US 8,789,756 B2
(45) Date of Patent: Jul. 29, 2014

(54) TEST ELEMENT CODING APPARATUSES, SYSTEMS AND METHODS

(75) Inventors: John T. Austera, Indianapolis, IN (US);
Abner D. Joseph, Carmel, IN (US);
Randall Riggles, Indianaoplis, IN (US);
Herbert Harttig, Neustadt (DE); Hans List, Hesseneck-Kailbach (DE); Bernd Roesicke, Mannheim (DE); Gerrit Kocherscheidt, Heddesheim (DE);
Bruno Thoes, Quierschied (DE);
Jean-Michel Ashour, Weinheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 378 days.

(21) Appl. No.: 12/944,390

(22) Filed: Nov. 11, 2010

(65) Prior Publication Data
US 2011/0132778 A1 Jun. 9, 2011

Related U.S. Application Data

(63) Continuation-in-part of application No. 12/197,806, filed on Aug. 25, 2008.

(30) Foreign Application Priority Data

Feb. 25, 2006 (EP) .................................... 0600380
Feb. 23, 2007 (WO) ................. PCT/EP2007/001605

(51) Int. Cl.
*G06K 7/10* (2006.01)
(52) U.S. Cl.
USPC ............ 235/462.05; 235/462.09; 235/462.08; 235/462.1; 235/462.13

(58) Field of Classification Search
USPC ............. 235/462.01, 462.05, 462.09, 462.08, 235/462.1, 462.11, 462.13, 462.32, 462.41, 235/462.42, 462.43, 486, 435, 439, 454, 235/494, 487
See application file for complete search history.

(56) References Cited

U.S. PATENT DOCUMENTS

| | | | |
|---|---|---|---|
| 4,105,926 A * | 8/1978 | Reno et al. .................... | 250/566 |
| 4,197,088 A * | 4/1980 | Meserol et al. ............... | 436/528 |
| 4,263,504 A | 4/1981 | Thomas | |
| 4,282,425 A | 8/1981 | Chadima, Jr. et al. | |
| 4,400,353 A * | 8/1983 | Meserol et al. ................ | 422/73 |
| 4,577,099 A * | 3/1986 | Goodman ..................... | 250/216 |

(Continued)

FOREIGN PATENT DOCUMENTS

| DE | 103 48 283 A1 | 5/2005 |
|---|---|---|
| DE | 103 60 786 B4 | 7/2005 |

(Continued)

OTHER PUBLICATIONS

International Search Report and Written Opinion, PCT/EP2007/001605, F. Hoffmann-LaRoche AG, The International Searching Authority/European Patent Office, Jul. 23, 2007.

(Continued)

*Primary Examiner* — Paultep Savusdiphol
(74) *Attorney, Agent, or Firm* — Krieg DeVault LLP

(57) ABSTRACT

Certain exemplary embodiments include a test element operable to receive a sample and to provide an indication of an analyte of the sample to a meter. In one form test element comprises a substrate and an optically readable pattern provided on the substrate which encodes information relating to the test element.

32 Claims, 17 Drawing Sheets

(56) References Cited

U.S. PATENT DOCUMENTS

| | | | |
|---|---|---|---|
| 4,592,893 A | 6/1986 | Poppe et al. | |
| 4,647,544 A * | 3/1987 | Nicoli et al. | 436/518 |
| 4,692,603 A | 9/1987 | Brass et al. | |
| 4,728,783 A | 3/1988 | Brass et al. | |
| 4,745,269 A | 5/1988 | Van Gils | |
| 4,754,127 A | 6/1988 | Brass et al. | |
| 4,782,221 A | 11/1988 | Brass et al. | |
| 4,786,792 A | 11/1988 | Pierce et al. | |
| 4,794,239 A | 12/1988 | Allais | |
| 4,874,936 A | 10/1989 | Chandler et al. | |
| 4,896,029 A | 1/1990 | Chandler et al. | |
| 4,939,354 A | 7/1990 | Priddy et al. | |
| 4,998,010 A | 3/1991 | Chandler et al. | |
| 5,053,609 A | 10/1991 | Priddy et al. | |
| 5,118,369 A | 6/1992 | Shamir | |
| 5,124,536 A | 6/1992 | Priddy et al. | |
| 5,128,526 A | 7/1992 | Yoshida | |
| 5,153,418 A | 10/1992 | Batterman et al. | |
| 5,189,292 A | 2/1993 | Batterman et al. | |
| 5,198,369 A * | 3/1993 | Itoh et al. | 436/534 |
| 5,203,591 A | 4/1993 | Treat | |
| 5,205,552 A | 4/1993 | Green, Jr. | |
| 5,223,701 A | 6/1993 | Batterman et al. | |
| 5,228,972 A * | 7/1993 | Osaka et al. | 204/415 |
| 5,235,172 A | 8/1993 | Oehlmann | |
| 5,243,655 A | 9/1993 | Wang | |
| 5,245,165 A | 9/1993 | Zhang | |
| 5,281,395 A * | 1/1994 | Markart et al. | 422/82.05 |
| 5,343,031 A | 8/1994 | Yoshida | |
| 5,369,261 A | 11/1994 | Shamir | |
| 5,393,967 A | 2/1995 | Rice et al. | |
| 5,439,649 A * | 8/1995 | Tseung et al. | 422/510 |
| 5,481,103 A | 1/1996 | Wang | |
| 5,554,841 A | 9/1996 | Kost et al. | |
| 5,569,607 A | 10/1996 | Simon et al. | |
| 5,591,956 A | 1/1997 | Longacre, Jr. et al. | |
| 5,612,524 A | 3/1997 | Sant'Anselmo et al. | |
| 5,683,786 A * | 11/1997 | Kavanaugh | 428/195.1 |
| 5,726,435 A | 3/1998 | Hara et al. | |
| 5,770,389 A * | 6/1998 | Ching et al. | 435/7.92 |
| 5,786,584 A * | 7/1998 | Button et al. | 235/462.15 |
| 5,825,015 A | 10/1998 | Chan | |
| 5,919,553 A * | 7/1999 | Kavanaugh | 428/195.1 |
| 5,945,341 A | 8/1999 | Howard, III | |
| 5,989,917 A * | 11/1999 | McAleer et al. | 436/46 |
| 6,016,961 A | 1/2000 | Hippenmeyer et al. | |
| 6,036,092 A | 3/2000 | Lappe | |
| 6,070,805 A | 6/2000 | Kaufman et al. | |
| 6,119,071 A | 9/2000 | Gorenflo et al. | |
| 6,121,599 A | 9/2000 | Traber | |
| 6,176,119 B1 * | 1/2001 | Kintzig | 73/53.01 |
| 6,234,392 B1 * | 5/2001 | Murakami | 235/462.12 |
| 6,260,763 B1 | 7/2001 | Svetal | |
| 6,378,702 B1 * | 4/2002 | Kintzig | 206/456 |
| 6,394,952 B1 | 5/2002 | Anderson et al. | |
| 6,409,740 B1 * | 6/2002 | Kuhr et al. | 606/182 |
| 6,413,213 B1 * | 7/2002 | Essenpreis et al. | 600/300 |
| 6,460,770 B1 | 10/2002 | Kucharczyk | |
| 6,669,092 B2 | 12/2003 | Leanheart et al. | |
| 6,770,487 B2 * | 8/2004 | Crosby | 436/518 |
| 6,773,671 B1 | 8/2004 | Lewis et al. | |
| 6,780,645 B2 * | 8/2004 | Hayter et al. | 436/8 |
| 6,814,844 B2 | 11/2004 | Bhullar et al. | |
| 6,819,422 B2 * | 11/2004 | Yamauchi | 356/344 |
| 6,879,399 B2 * | 4/2005 | Yamauchi | 356/344 |
| 6,883,711 B2 | 4/2005 | Patton | |
| 6,981,644 B2 | 1/2006 | Cheong et al. | |
| 6,988,996 B2 * | 1/2006 | Roe et al. | 600/584 |
| 7,020,327 B2 | 3/2006 | Tack-don et al. | |
| 7,097,103 B2 | 8/2006 | Tseng | |
| 7,128,265 B2 * | 10/2006 | Silverbrook et al. | 235/462.08 |
| 7,131,596 B2 * | 11/2006 | Lapstun et al. | 235/494 |
| 7,154,592 B2 * | 12/2006 | Reynolds et al. | 356/39 |
| 7,186,566 B2 * | 3/2007 | Qian | 436/524 |
| 7,233,340 B2 * | 6/2007 | Hughes et al. | 345/629 |
| 7,267,799 B1 * | 9/2007 | Borich et al. | 422/82.05 |
| 7,344,081 B2 | 3/2008 | Tseng | |
| 7,487,914 B2 | 2/2009 | Yoon et al. | |
| 7,674,232 B2 * | 3/2010 | Boecker et al. | 600/583 |
| 7,695,608 B2 | 4/2010 | Kim et al. | |
| 7,717,863 B2 * | 5/2010 | Freeman et al. | 600/583 |
| 7,731,900 B2 * | 6/2010 | Haar et al. | 422/66 |
| 7,785,272 B2 * | 8/2010 | Roe et al. | 600/584 |
| 7,796,266 B2 * | 9/2010 | Cohen et al. | 356/440 |
| 7,803,318 B2 * | 9/2010 | Hubner et al. | 422/400 |
| 7,841,992 B2 * | 11/2010 | Freeman et al. | 600/583 |
| 7,850,622 B2 * | 12/2010 | Freeman et al. | 600/583 |
| 7,892,183 B2 * | 2/2011 | Boecker et al. | 600/583 |
| 7,901,362 B2 * | 3/2011 | Freeman et al. | 600/583 |
| 7,959,581 B2 * | 6/2011 | Calasso et al. | 600/583 |
| 7,981,055 B2 * | 7/2011 | Freeman et al. | 600/583 |
| 8,016,774 B2 * | 9/2011 | Freeman et al. | 600/583 |
| 8,273,579 B2 * | 9/2012 | Morrison | 436/164 |
| 2001/0042789 A1 | 11/2001 | Krichever et al. | |
| 2001/0045355 A1 * | 11/2001 | Gephart et al. | 204/400 |
| 2002/0030817 A1 | 3/2002 | Matsumoto | |
| 2004/0043502 A1 * | 3/2004 | Song et al. | 436/172 |
| 2004/0170309 A1 * | 9/2004 | Hughes et al. | 382/128 |
| 2004/0195330 A1 * | 10/2004 | Silverbrook et al. | 235/454 |
| 2004/0195341 A1 * | 10/2004 | Lapstun et al. | 235/494 |
| 2004/0241752 A1 * | 12/2004 | Anderson et al. | 435/7.1 |
| 2005/0094263 A1 * | 5/2005 | Vaccarelli | 359/396 |
| 2005/0187444 A1 * | 8/2005 | Hubner et al. | 600/322 |
| 2005/0243321 A1 * | 11/2005 | Cohen et al. | 356/432 |
| 2005/0244952 A1 * | 11/2005 | Cohen | 435/287.2 |
| 2005/0244953 A1 * | 11/2005 | Cohen | 435/287.2 |
| 2006/0002636 A1 * | 1/2006 | Torre-Bueno et al. | 382/305 |
| 2006/0019265 A1 * | 1/2006 | Song et al. | 435/6 |
| 2006/0104499 A1 * | 5/2006 | Zahniser et al. | 382/141 |
| 2006/0243804 A1 | 11/2006 | Christoffersen et al. | |
| 2007/0025877 A1 * | 2/2007 | Hansen | 422/68.1 |
| 2007/0048815 A1 * | 3/2007 | Song | 435/18 |
| 2007/0092408 A1 * | 4/2007 | Angros | 422/99 |
| 2007/0121113 A1 * | 5/2007 | Cohen et al. | 356/432 |
| 2007/0273928 A1 | 11/2007 | Robinson et al. | |
| 2008/0056952 A1 * | 3/2008 | Angros | 422/99 |
| 2008/0121789 A1 | 5/2008 | Augstein et al. | |
| 2009/0042306 A1 | 2/2009 | Reynolds et al. | |
| 2009/0212109 A1 | 8/2009 | Harttig et al. | |
| 2009/0294544 A1 | 12/2009 | Walmsley et al. | |
| 2010/0072272 A1 * | 3/2010 | Angros | 235/375 |
| 2010/0110541 A1 * | 5/2010 | Angros | 359/397 |

FOREIGN PATENT DOCUMENTS

| | | | |
|---|---|---|---|
| DE | 10 2004 051 124 B3 | 12/2005 | |
| EP | 1 288 653 A1 | 3/2003 | |
| EP | 1 424 040 A1 | 6/2004 | |
| EP | 1 826 705 A1 | 8/2007 | |
| JP | 59 121578 | 7/1984 | |
| WO | WO 02/088739 A1 | 11/2002 | |
| WO | WO 2009/020690 A1 | 2/2009 | |
| WO | WO 2010/015843 A1 | 2/2010 | |
| WO | WO 2010/042435 A1 | 4/2010 | |
| WO | WO 2010/048277 A2 | 4/2010 | |

OTHER PUBLICATIONS

European Search Report, EP1826705A1, Application No. EP06003880, F. Hoffmann-LaRoche AG, Sep. 21, 2006.

Bar Code 1 2-Dimensional Bar Code Page; http://www.adams1.com/pub/russadam/stack.html, Adams Communications, pp. 1-11, 1995-2005.

* cited by examiner

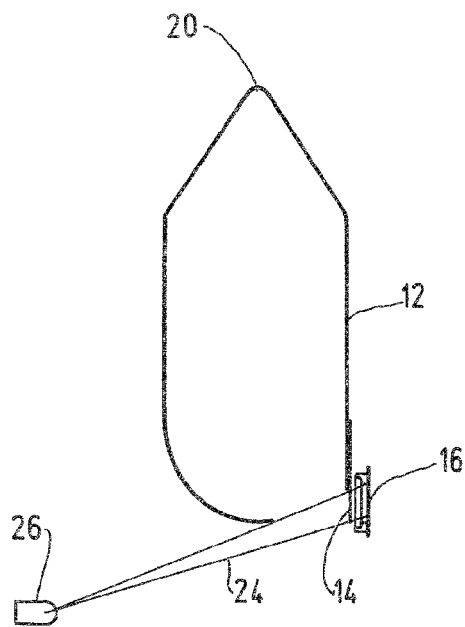
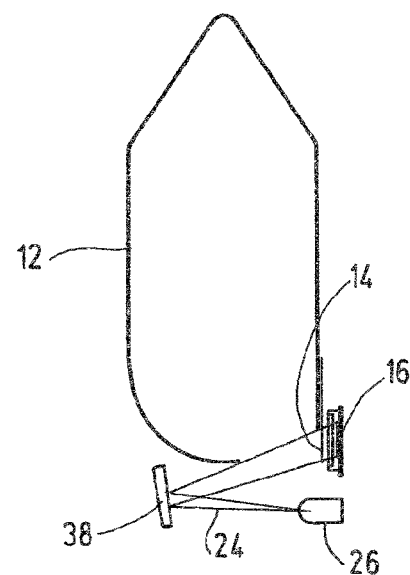
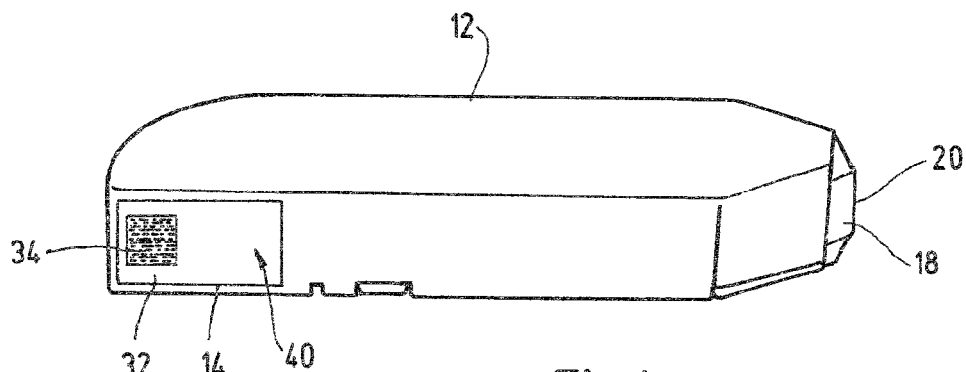
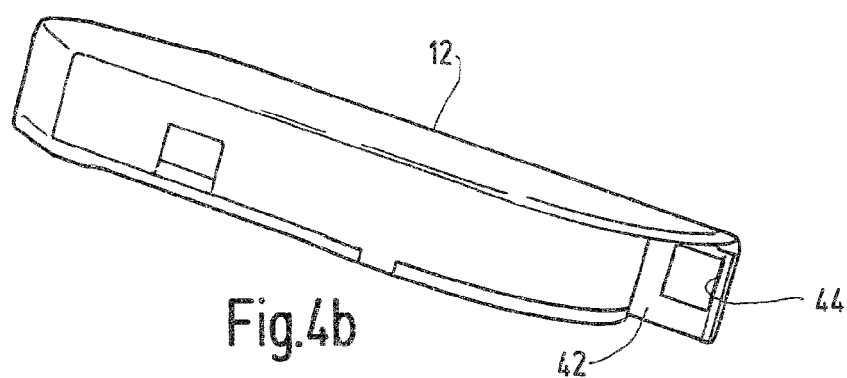

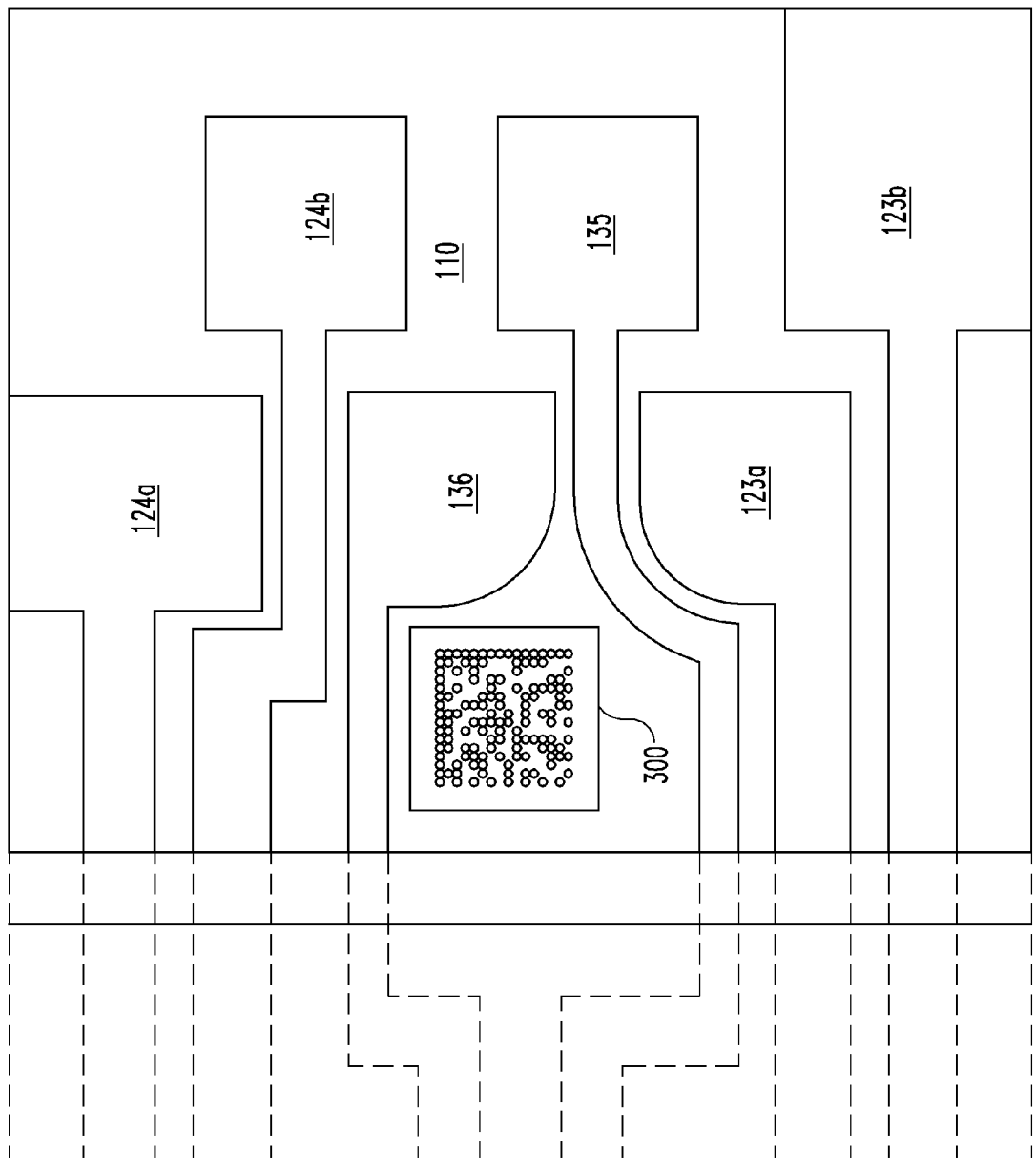

TEST ELEMENT CODING APPARATUSES, SYSTEMS AND METHODS

PRIORITY

The present application is a continuation in part of U.S. application Ser. No. 12/197,806 filed Aug. 25, 2008 which is based on and claims priority to PCT Application No. PCT/EP2007/001605, filed Feb. 23, 2007, which claims the priority benefit to European Application No. 06003880.9, filed Feb. 25, 2006, each of which is hereby incorporated by reference in its entirety and the benefit of each of which is claimed.

BACKGROUND

There are significant and increasing needs to measure analytes present in a sample. For example, patients with diabetes can benefit from measurement of their blood glucose. Those potentially at risk of heart disease can benefit from measurement of cholesterols and triglycerides among other analytes. These are but a few examples of patient benefit from analyte measurement in biological samples. Advancements in the medical sciences are identifying a growing number of analytes including molecules, lipids, carbohydrates, amino acids, antibodies, proteins, nucleic acids, peptides, viruses, bacteria, markers, drugs, toxins, and other analytes which could be measured to identify a number of diseases, disorders and conditions. There is also a need for measurement of other analytes including contaminants, impurities, and toxins in a variety of samples. Present approaches to analyte measurement are subject to a number of drawbacks, limitations, disadvantages and problems. There is a need for the unique, beneficial and inventive solutions disclosed herein.

SUMMARY

For the purposes of clearly, concisely and exactly describing exemplary embodiments of the invention, the manner and process of making and using the same, and to enable the practice, making and use of the same, exemplary embodiments will now be summarized and described in detail, and reference will be made to the exemplary embodiments illustrated in the figures and specific language will be used to describe the same. It shall nevertheless be understood that no limitation of the scope of the invention is thereby created, and that the invention includes and protects such alterations, modifications, and further applications of the exemplary embodiments as would occur to one skilled in the art.

Certain exemplary embodiments include apparatuses comprising a test element operable to receive a sample and to provide an indication of an analyte of the sample to a meter. The test element comprises a substrate and an optically readable pattern provided on the substrate and encoding information relating to the test element. The substrate has an optical transmittance relative to a light source. The optically readable pattern comprises one or more opaque marked portions and one or more unmarked portions. The optically readable pattern is readable under stationary transillumination by the light source as a shadow image projected onto a sensor. Certain exemplary embodiments comprise a transillumination optical pathway through a test element defined by and consists essentially of the substrate and the optically readable pattern.

Certain exemplary embodiments include systems comprising a test element configured to receive a sample and to provide an indication of an analyte of the sample. The test element comprises a transparent or translucent substrate, an opaque pattern provided on the substrate to encode information relating to the test element, and an optical pathway through the test element consisting essentially of the substrate and the pattern. The systems may further comprise a measurement device configured to interface with the test element to receive the indication of the analyte of the sample. The measurement device comprises an optical source configured to provide light to the optical pathway and an optical sensor configured to receive light from the optical pathway.

Certain exemplary embodiments include methods comprising providing a meter including a light source and an optical sensor and providing a test element. The test element comprises a substrate, a matrix pattern provided on the substrate, and an optical pathway consisting essentially of the substrate and the matrix pattern. The optical pathway comprises one or more regions having optical transmittance relative to the light source and one or more regions being substantially opaque relative to the light source. The methods may further comprise transferring information encoded by the matrix pattern to the meter by directing light from the light source to the optical pathway and detecting light emitted from the optical pathway with the detector. The methods may further comprise testing a sample for an analyte using the test element, the meter, and the transferred information.

In certain exemplary embodiments the test element comprises an electrochemical test element. In certain exemplary embodiments the test element comprises a sample chamber, a reagent, a working electrode, and a counter electrode, and the test element is operable to receive a sample in the sample chamber, react the sample with the reagent, and provide an indication of an analyte of the sample when the working electrode and the counter electrode are electrically coupled with the meter.

In certain exemplary embodiments the optically readable pattern comprises an opaque material disposed on a surface of the substrate and defining one or more void regions exposing the substrate. In certain exemplary embodiments the optically readable pattern is formed by laser ablation of opaque material. In certain exemplary embodiments the optically readable pattern is formed by inkjetting opaque material. In certain embodiments the opaque material is conductive material Certain exemplary embodiments comprise an optically readable pattern having an information density of about 64 bits per square millimeter or greater. Certain exemplary embodiments comprise an optically readable pattern having an information density of about 96 bits per square millimeter or greater. In certain exemplary embodiments the pattern comprises an area less than about one square millimeter.

Certain exemplary embodiments comprise a meter configured to receive the test element and having a light source configured to illuminate a portion of a first surface of the test element received by the meter, and a sensor configured to detect light transmitted through the test element. In certain exemplary embodiments a light path between the optical source and the test element is folded. In certain exemplary embodiments the optical source provides light to the optical pathway at a first surface of the test element and the pattern is provided on a second surface of the test element substantially opposing the first surface. In certain exemplary embodiment the optical source is positioned on a first side of the test element and the detector is positioned on a second side of the test element. In certain exemplary embodiments a sample is provided to the test element and an electrical response of the test element is evaluated by a meter based at least in part upon information transferred to the meter from an optically readable pattern on the test element.

BRIEF DESCRIPTION OF THE FIGURES

FIGS. 3 and 4 show further arrangements of a reading device on a disposable cassette in a diagram corresponding to FIG. 1.

FIGS. 4a and b show the disposable cassette according to FIG. 1 in two perspective views of the narrow side.

FIG. 9b is a perspective view of the assembled exemplary test element of FIG. 9a.

FIG. 9c is a top close up view of one end of the exemplary test element of FIG. 9b showing a coding feature.

DETAILED DESCRIPTION OF EXEMPLARY EMBODIMENTS

Figure 1:
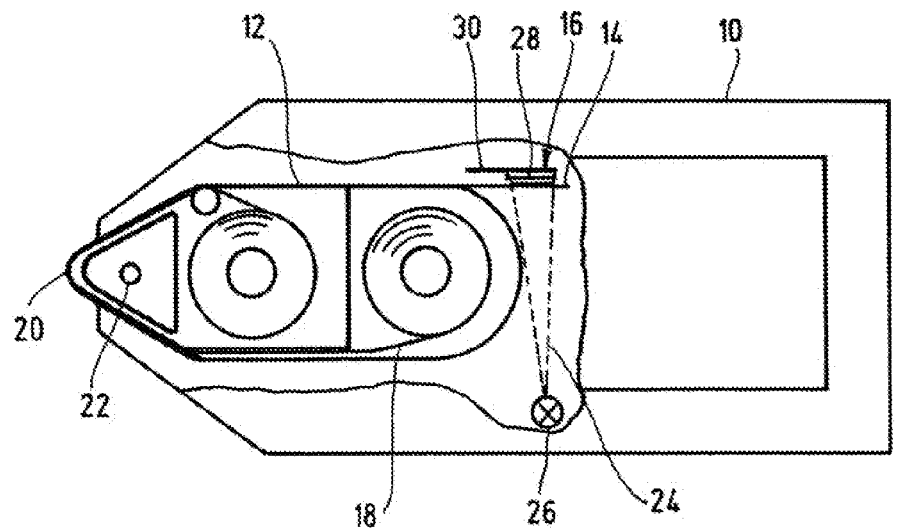
FIG. 1 shows a measuring device with a replaceable disposable cassette and an optical reading device for an information carrier on the cassette in a partially cut-out side-view.

The exemplary measuring device 10 shown in FIG. 1 enables the use of a test tape cassette 12 as an analytical disposable for carrying out, in this embodiment, blood glucose tests in which test-specific information on an information carrier 14 on the casette 12 can be read out by means of the device's own reading device 16.

The test tape casette 12 contains a test tape 18, sections of which are provided with test fields to which blood can be applied to a tip 20 protruding from the device 10 in order to locally determine a blood glucose value by means of the measuring device 22. A plurality of tests can thus be carried out by winding on the test tape 18, before the cassette 10 is used and has to be replaced. Reference is for example made to EP 1424040 and DE 10348283 with regard to further details of such hand-held devices, the disclosures of which are hereby incorporated by reference herein in their entireties.

In principle, the use of the information carrier and the associated reading device described here is not restricted to such test tape cassettes. Other diagnostic or analytical test units can also be provided with them and in particular also test strips such as those that are currently used to examine body fluids. Their use is also advantageous in other medical disposables e.g. dialysers, tube sets, infusion containers and suchlike which are used in devices and also for disposables in other fields of application such as for example colour, printing, lubricant or additive cartridges, grinding or cutting implements, sample or tool carriers, moulds or receivers such as e.g. printing screens.

Figure 2:
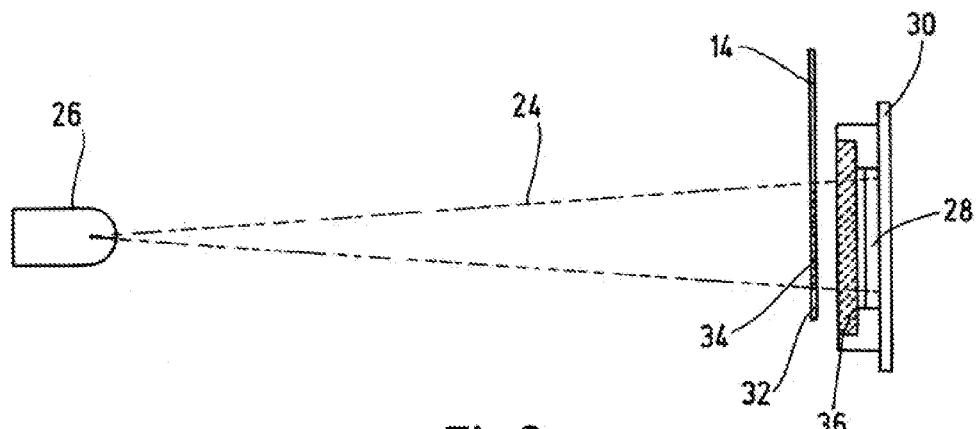
FIG. 2 shows an enlarged diagram of the reading device and the information carrier according to FIG. 1.

As shown in FIGS. 1 and 2, the information carrier 14 as part of the cassette 10 is located in the optical path (light beam 24) of the reading device 16. This device comprises a light source 26 and a generally flat sensor 28 on a circuit board of the device 30. In order to make the system as simple as possible, a scanning relative movement of the reading light and the information carrier 14 is not employed and instead a simple shadow image of the code on the information carrier is detected. For this purpose the information carrier 14 comprises a substrate 32 which is generally transparent or translucent to the light beam and a graphic code 34 applied thereto which is described in more detail below. This code is thrown as a shadow image through the entry window 36 onto the receiving surface of the sensor 28 when it is read by the stationary i.e. spatially unmoved light beam 24 without using an imaging optical system.

In order to in this case achieve the highest possible resolution, the light source 26 comprises a point light source and is arranged at a large distance to the information carrier 14 compared to its distance from the sensor 28, where in the latter case it is desirable to have a direct contact between the substrate 32 and entry window 36.

A point light source 26 is typically regarded as a light source which is characterized by small dimensions of the light-emitting area, or which has comparable emission characteristics as a result of optical elements. Light-emitting diodes (LED) are typically suitable for this, but filament lamps, laser diodes, gas discharge lamps and suchlike as well as light guides can also be used in a suitable configuration. The wavelength of the light for illumination is generally only limited by the sensitivity of the optical sensor and the material properties of the information carrier 14. Visible light can be used, including red light, because the most cost-effective LEDs operate in this wavelength range.

The smaller the dimensions and the larger the distance of the light source 26, and the smaller the distance of the sensor 28 from the information carrier 14, the sharper will be the image of the code module on the surface of the sensor 28. A sharp image enables a reliable detection already at a low over-sampling. Over-sampling denotes the multiple of pixels which is required to reliably detect a code element. Single over-sampling means that one pixel per code element is available on the sensor. Double over-sampling means that two pixels are available for each edge length or line thickness of the code 34. The higher the chosen over-sampling, the lower are the required imaging qualities and position accuracies for a reliable reading. However, the number of pixels increases quadratically with the over-sampling. Thus, the amount of data that has to be read, stored and processed also increases. This generally requires hardware components of an adequate size as well as longer processing times and/or faster processors.

In one embodiment, the light-sensitive sensor comprises a CMOS sensor; alternatively a CCD sensor can also be used. The light-sensitive surface of such sensors generally comprises a plurality of pixels which individually record the local brightness. When the code 34 is illuminated by the point light source 26, the modules or elements of the code 34 impede the passage of light whereas the light impacts the light-sensitive sensor 28 almost unhindered through the transparent/translucent substrate 32. The differences in brightness generated in this manner are read by electronics of the reading device 16 and can be processed to form a total image of the code 34. The electronics can also comprise components for further image processing in order to decode the code 34 into alphanumeric characters.

The position of the code 34 relative to the sensor 28 can tolerate relatively large deviations. The deviations in the direction of the width and the height of the code can be compensated by selecting a light-sensitive area of the sensor 28 which is enlarged compared to the code. The effect of deviations in the distance between the code 34 and the sensor 28 can be kept small by the small dimensions and a large spacing of the point light source 26 and the omission of distorting optical components in the light path.

In order to further reduce the positioning tolerances, the sensor assembly 28, 36 can be seated in a flexible mounting 30. This minimizes deviations in the lateral position and level of the information carrier 14 so that a smaller light-sensitive area of the sensor 28 is sufficient. In particular a spring mounting enables a contact between the information carrier 14 and the surface of the sensor 28 without the risk of damage even when the casette 12 is inserted into a device holder that has tolerances.

As described above the point light source 26 may be positioned at a large distance from the information carrier 14. In this connection it has turned out that an orthogonal alignment relative to the sensor area is necessary. In accordance with FIG. 3a the light source 26 can also be laterally displaced thus enabling a useful exposure to light without interfering contours occurring due to the disposable 12. As shown in FIG. 3b the incident path of the light beam 24 can be folded by a mirror 38 or another suitable optical element in order to minimize the overall length of the device. Such an optical element can also have imaging properties which form a virtual point light source from an expanded light source.

As shown in FIG. 4a the information carrier 14 can be glued onto the casette 12 in the form of an adhesive label 40. The adhesive area can be omitted in the area of the code 34 or a transparent adhesive is used. The rear view of FIG. 4b shows that a window or an opening 44 spanned by the label 40 is provided in a projecting support tab 42 of the casette 12 and thus allows an unhindered illumination of the code 34 from the rear side in the configurations shown in FIG. 3.

In principle it is also possible that the light source 26 is effectively positioned within the object to be coded for example by using optical elements such as light guides for a suitable light guidance. It is also conceivable that a wall of the object is made as transparent or translucent as the substrate 32 thus enabling a transillumination of the code 34.

The code 34 can thus be generated on the object 12 to be coded itself or on a label 40 which is joined to the object 12 in the production process. Printing processes such as thermotransfer printing, screen printing, offset printing, laser printing and inkjet come into consideration for the production of the code 34. In addition laser engraving, laser ablation, film exposure and development, sputtering, sublimation processes and other suitable processes can also be used. The contrast for displaying the code 34 can thus be generated by dyes or pigments such as those contained in printing colours or photographic films, by metal layers, by changes in materials such as colouration, charring, by light-scattering phase interfaces (e.g. pores) or in other suitable ways. The code can either be configured as a positive with dark modules or inverted as a negative with transparent modules. The code can be a one-dimensional or two-dimensional barcode, line code, point code or a derivative thereof. A so-called data matrix code (ECC200) is preferably used in the embodiment described in the following. Further details on data matrix codes can for example be found in the U.S. Pat. Nos. 4,939,354; 5,053,609; 5,124,536; the disclosures of each of which are hereby incorporated herein by reference.

Figure 5:
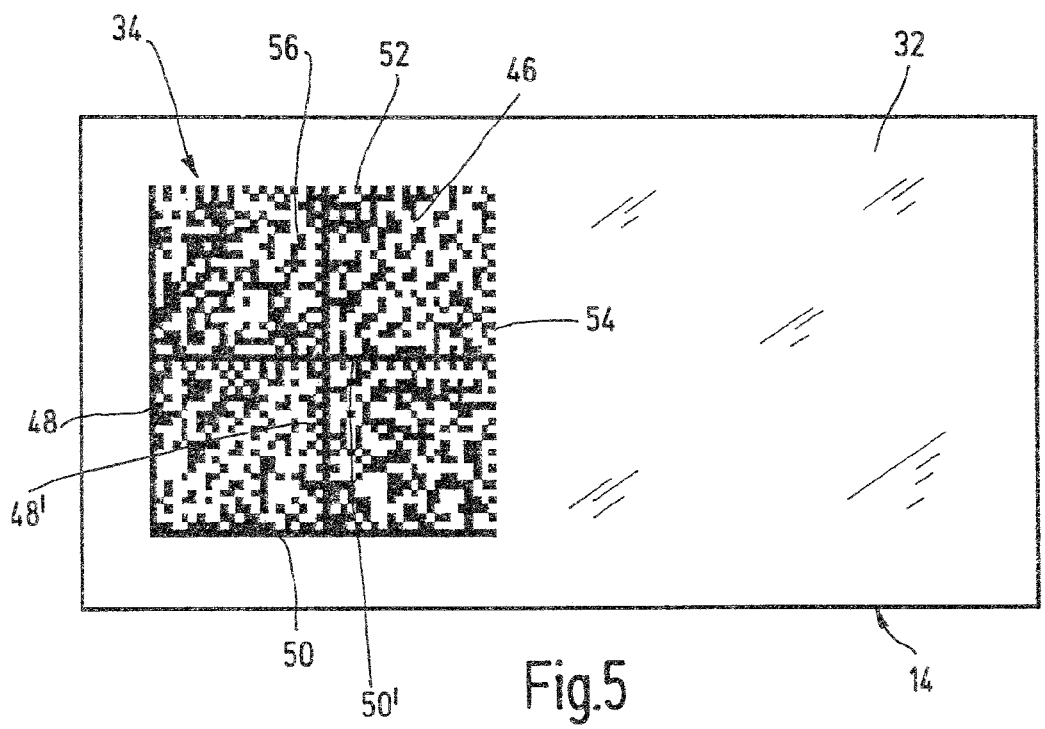
FIG. 5 shows an information carrier comprising a transparent substrate and a two-dimensional data matrix code.

FIG. 5 shows an information carrier 14 comprising a transparent or translucent substrate 32 and a two-dimensional graphic code 34 in the form of a data matrix code that is applied thereto. This code comprises a quadratic matrix of dark grid modules 46. In order to determine the orientation and density of the modules, a continuous dark line 50 or column 48 is provided on two adjoining edges or sides of the square whereas the other two edges 52, 54 have alternating dark and light modules where the right upper corner is always light. This so-called alignment pattern can, as shown, also be repeated in the inside of the code area 56 (line 50' or column 48').

Data matrix codes 34 generally have angle tolerance, i.e. they can be read and evaluated when rotated by virtually any angle relative to a reference alignment. When such a code is read in direct contact as described above, it is necessary to use a sensor 28 whose optically sensitive area is larger than the edge length of the code at least by the horizontal and vertical position tolerance. If the sensor is not aligned parallel to the edges of the code then, instead of the edge length of the code, the projection of the diagonals has to be taken into account which is at most 1.41-times the edge length at any angular position. If only small angles of rotation are expected, it is not necessary to completely form an image of the code on the optically sensitive area of the sensor when utilizing the error tolerance of a data matrix code or of a similar code with error correction.

Figure 6:
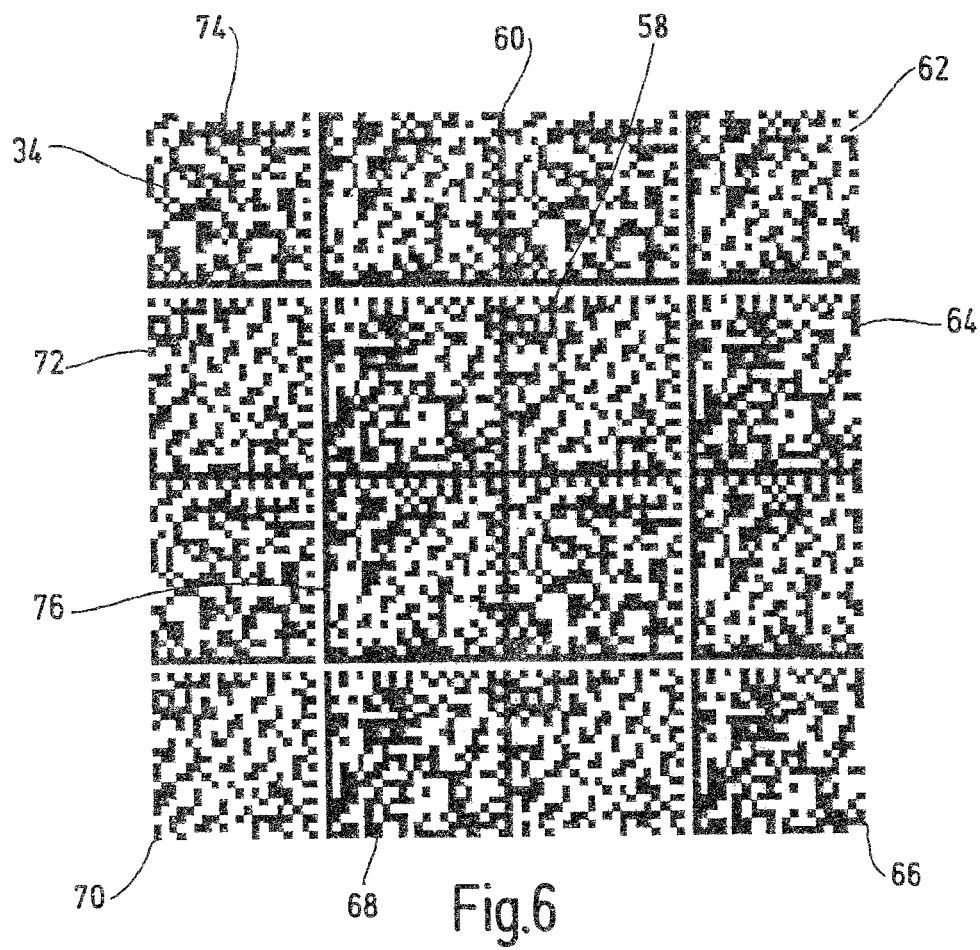
FIG. 6 shows an embodiment of a matrix code with a base code area and bordering copy code areas.

In order to create a position-tolerant code in this connection which can also be reliably read by smaller and thus inexpensive sensors, an extensive code area is provided as shown in FIG. 6. In this case the code 34 has a base code area 58 corresponding to the diagram in FIG. 5 which is framed by several adjacent copy code areas 60, 62, 64, 66, 68, 70, 72, 74. The copy code areas 60-74 are each displaced relative to the base code area 58 only in one direction generally vertically, generally horizontally and/or generally diagonally, only to the extent that they adjoin the borders of the base code without overlap while forming a quiet zone 76 of at least the dimensions (width or height) of a code element. The copy code areas are in this case formed by the border segments of the base code area which face away vertically, horizontally and diagonally. For example the copy code area 60 corresponds to the lower half of the base code area 58 whereas the copy code area 66 corresponds to the left upper quarter of the base code area 58.

Due to the presence of copies of the base code, it is possible for an optically sensitive sensor 28 of the size of the base code area 58 to detect all information of the base code irrespective of the relative deviation in position. This is of course providing that the dimensions of the code 34 are so large that the detection area of the sensor 28 does not extend beyond the edge of the code 34.

The base code is reconstructed by the reading device 16 firstly determining the origin of the coordinate system of the code image. This is firstly explained for an embodiment with a quiet zone. The following convention applies to the explanation. An illuminated pixel yields the value 1, a shaded pixel yields the value 0. Intermediate values are prevented by an upstream discriminator, e.g. a Schmitt trigger.

Firstly all sums of the columns and lines are added up and minima and maxima of the means are determined. These first minima and maxima are brought onto the absolute minima and maxima of the means by incremental virtual rotation of the pixel data. At the origin of the coordinate system of the code image several columns with a maximum value of the column mean adjoined by several columns with a minimum value of the column mean intersect in each case with several lines with a maximum value of the line mean adjoined by several lines with a minimum value of the line mean. The intersection of the crossovers from the minimum value to the maximum value in the relevant columns and lines is the origin. If the reading device 16 identifies more than one such intersection, then the intersection with the smallest x value and the smallest y value of the coordinates on the sensor 28 is determined as the origin of the coordinate system of the code image.

In the code image of FIG. 6 a column or line with alternating light and dark code elements is located next to each of the quiet zones 76. When the base code is reconstructed in a processor (not shown) the average distance between a light/dark transition is determined in the x direction as well as in the y direction. Thus, the number of pixels that correspond to the edge length of a code element is known. Taking into account the determined rotation and the edge length, lines of pixel values are transferred into a complete orthogonally aligned code image in a memory starting at the origin. The decoding algorithms are applied to this virtual code image in order to obtain the code content in a digitally utilizable form.

Figure 7:
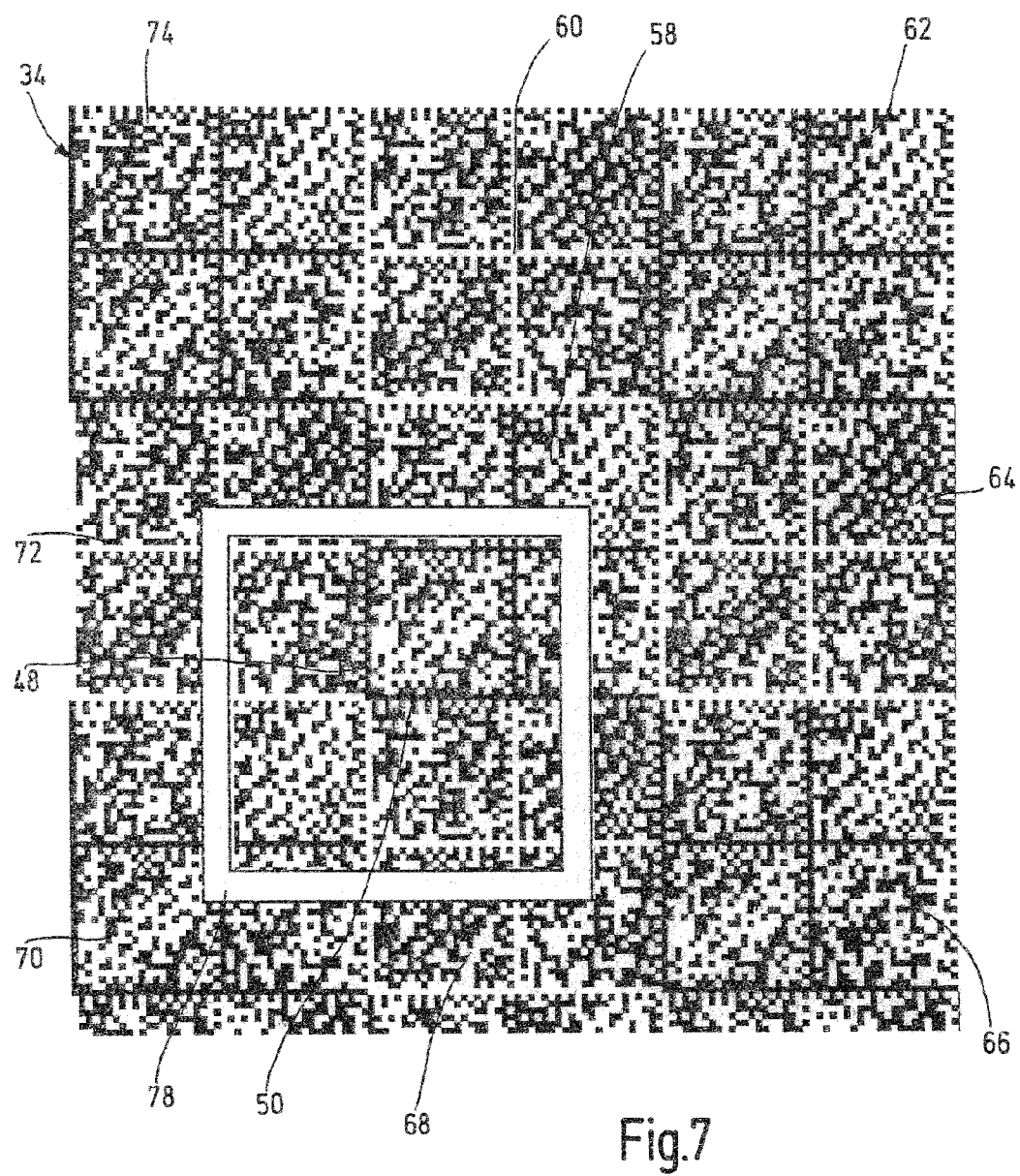
FIG. 7 shows a further embodiment of the matrix code with a base code area and alternating inverted and non-inverted copy code areas and a sensor window of the reading device symbolized therein.

In the embodiment example shown in FIG. 7 the base code area 58 is framed by complete copies 60-74. Starting from the base code area 58, the copies 60-74 are shifted vertically, horizontally and diagonally to such an extent that they exactly join the code edges without gaps and without overlaps. This results in a 2D code with three times the edge length and nine times the area of the base code area 58. In order to be able to simply detect the alignment pattern while avoiding quiet zones, the copies 60-74 are alternately inverted and non-inverted starting from the base code area 58. The copies 60, 64, 68, 72 are referred to as inverted in which the modules that are dark in the original 58 are light and the modules that are light in the original are dark. This thus results in a chessboard-like pattern of non-inverted and inverted base codes.

When the alignment patterns 48,50 of the base code area 58 are dark, the alignment patterns of the inverted copies are light and are thus clearly distinguishable. Dark angles from the alignment patterns 48,50 are present at the left lower edge of a non-inverted code area 58, 62, 66, 70, 74. In contrast light angles are present at the left lower edge of an inverted code area 60, 64, 68, 72. Equally there is an intersection of dark lines inside a non-inverted code area and an intersection of light lines inside an inverted code area. There is a dark T-formation at the edge of a non-inverted code area and a light T-formation at the edge of an inverted code area. This information enables the base code area 58 to be reconstructed and provided for the decoding at any position of the sensor 28 shown in FIG. 7 by a reading window 78 provided it does not extend beyond the edge of the code 34.

The code copying according to the invention is not only limited to the contact mode described above, but can also be advantageously used when reading codes 34 by an imaging optical system in order to increase the positioning tolerance. Also in this case it may be necessary when replacing a disposable 12 to exactly position the information carrier to be read within a certain tolerance. Especially in the case of readers that are permanently installed in the device that have to read only a few different code types, the use of the proposed code copies allows the use of smaller and thus less expensive optical sensors.

Figure 8:
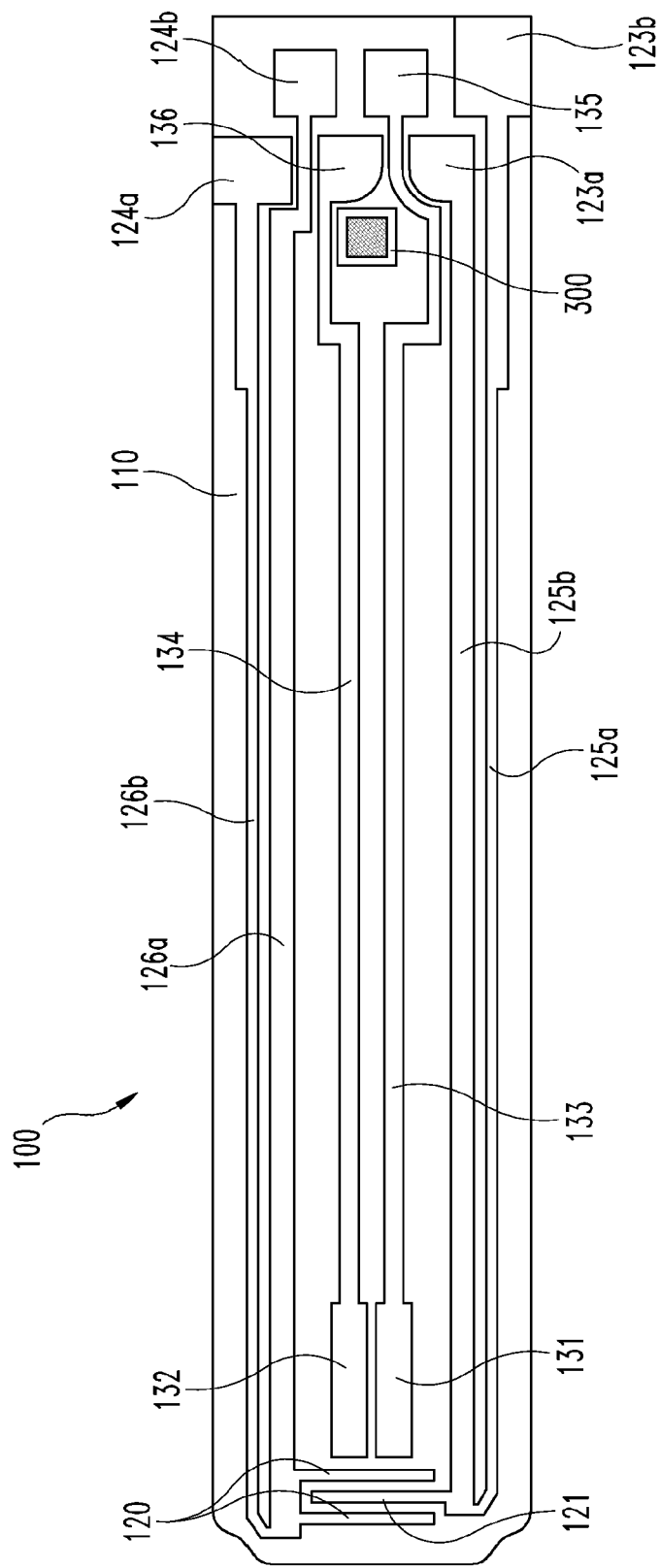
FIG. 8 is a top view of a portion of an exemplary test element.

FIG. 8 illustrates an exemplary test element 100 including a substrate 110 and an arrangement of electrically conductive material provided on the substrate 110. The substrate 110 preferably comprises polyethylene terephthalate ("PET"). The substrate 110 may also comprise other materials including, for example, polyesters or other polymeric or thermoplastic materials. One exemplary PET material comprises Melinex® brand PET from DuPont. The substrate may also be any suitable substrate that has the optical (e.g. transparent or translucent) characteristics in accordance with certain particular embodiments set forth herein.

In certain exemplary embodiments the substrate 110 is selected to have particular optical characteristics, for example, optical transmittance, reflectance, and/or absorptance characteristics at one or more predetermined electromagnetic radiation wavelengths or wavelength ranges. In some exemplary embodiments the optical characteristics are selected for the visible light wavelengths. In some exemplary embodiments the optical characteristics are selected for the infrared wavelengths. In general, the transmissive optical characteristics of substrates are affected by the thickness of the substrate and the coloring or clarity of the material comprising substrate (e.g., white PET, translucent PET and transparent PET generally exhibit different transmittance characteristics for given thickness), and the percentage of transmittance is relative to the intensity and wavelength of the light transmitted therethrough. Exemplary substrates are preferably selected to have transmissive optical characteristics sufficient to allow a given light source to be detected after passing through the substrate and to allow information from a pattern provided on the substrate be modulated onto light travelling through the substrate at the location of the pattern. In certain exemplary embodiments selected optical characteristics are exhibited or exposed substantially throughout the test element. In certain exemplary embodiments selected optical characteristics are exhibited or exposed in a portion of the overall test element, for example, in a portion designated for optical interrogation or pattern recognition.

In one embodiment, the material provided on substrate 110 comprises material that can be coated on the substrate and ablated to define electrodes and/or code patterns, such as gold or a gold alloy. Additional materials that may be used include platinum, palladium, iridium, or alloys of thereof. Further non-limiting examples of material which may be provided on substrate 110 include aluminum, carbon (such as graphite), cobalt, copper, gallium, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds thereof.

FIG. 8 illustrates an embodiment of a conductive pattern that may be useful for test elements provided for an electrochemical fluid analysis system. Other embodiments of conductive patterns will be understood by persons of ordinary skill in the art, particularly based on the state of the art, which are also useful in the context of test elements according to the present invention, and thus the scope of the present invention should not be limited to the illustrated embodiments of a test element described herein except as may be expressly recited in the claims. As illustrated in FIG. 8, the electrically conductive material is arranged on substrate 110 to provide a number of electrically conductive pathways. Particular arrangements of electrically conductive material, such as the arrangement illustrated in FIG. 8, may be provided using a number of techniques including chemical vapor deposition, laser ablation, lamination, screen-printing, or photolithography and combinations of these and other techniques. One illustrated electrically conductive pathway includes working electrode 121, working electrode contact pads 123a and 123b and conductive trace portions 125a and 125b which extend between and electrically couple working electrode 121 and working electrode contact pads 123a and 123b.

Another electrically conductive pathway illustrated in FIG. 8 includes counter electrode 120 (illustrates as comprising dual prongs), counter electrode contact pads 124a and 124b, and conductive trace portions 126a and 126b which extend between and electrically couple counter electrode 120 and counter electrode contact pads 124a and 124b.

A further electrically conductive pathway illustrated in FIG. 8 includes sample sufficiency electrode 131, sample sufficiency contact pad 135 and conductive trace portion 133 which extends between and electrically couples sample sufficiency electrode 131 and sample sufficiency contact pad 135. Another illustrated conductive pathway includes sample sufficiency electrode 132, sample sufficiency contact pad 136 and conductive trace portion 134 which extends between and electrically couples sample sufficiency electrode 132 and sample sufficiency contact pad 136. The sample sufficiency electrodes 131, 132 may be employed using known techniques for determining the sufficiency of filling a sample chamber (described below).

Also provided on substrate 110 is a coding feature 300 that comprises a pattern configured to encode information which can be transferred to a meter upon the test element being coupled with the meter. As illustrated in FIG. 8 coding feature 300 is positioned apart from, but proximate the test element contact pads. In additional exemplary embodiments, coding feature 300 is positioned in other locations including, for example, on the opposite surface of substrate 110 as the test element contact pads, or on a spacer member or cover member placed over substrate 110. Coding features 300 comprises an example of an optically readable pattern provided on substrate 110 which encodes information relating to test element 100. In certain embodiments coding feature 300 comprises an optically readable data matrix pattern. In certain embodiments coding feature comprises one or more opaque marked portions and one or more unmarked portions. The opaque marked portions may be provided with additive techniques (e.g. applying material such as by inkjetting) subtractive techniques (e.g., selective ablation of one or more features to define opaque marked portions) or combinations of additive and subtractive techniques. Marked portions may positively marked portions (e.g. areas where material remains over a substrate) or negatively marked portions (e.g., areas where material is absent from a substrate). The information encoded by the is readable under stationary transillumination by a light source as a shadow image projected onto a sensor Additional aspects, features, alternatives and variations of coding feature 300 are described below in connection with FIGS. 10a, 10b, 11a and 11b.

During a test operation involving test element 100, working electrode contact pads 123a and 123b may be coupled to working electrode terminals of a meter, counter electrode contact pads 124a and 124b may be coupled to counter electrode terminals of a meter, and sample detect contact pads 135 and 136 may be coupled to respective sample detect terminals of a meter. A sample to be analyzed may be provided to test element 110, for example, by introducing the sample into a sample chamber. The meter and test element 100 may be used to check alignment of the test element relative to the meter, to perform failsafe or error checking functions, for example, verifying the integrity of conductive pathways by testing for expected electrical characteristics between working electrode contact pads 123a and 123b or counter electrode contact pads 124a and 124b, to perform fill detection and sample sufficiency detection functions between pads 135, 136, and to perform electrochemical analysis functions such blood glucose concentration measurement or detection or measurement of other analytes.

Figure 9A:
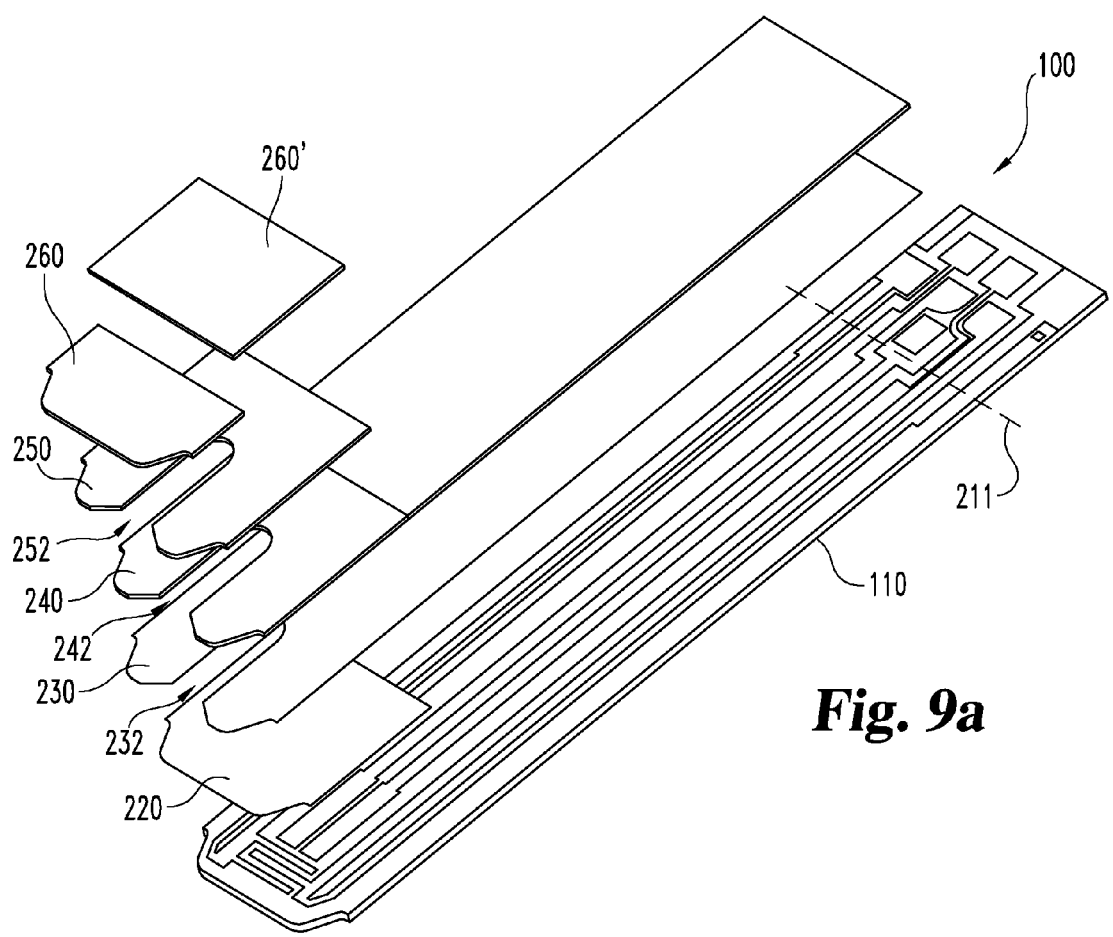
FIG. 9a is an exploded isometric view of the exemplary test element of FIG. 8 illustrating additional features.
Figure 9B:
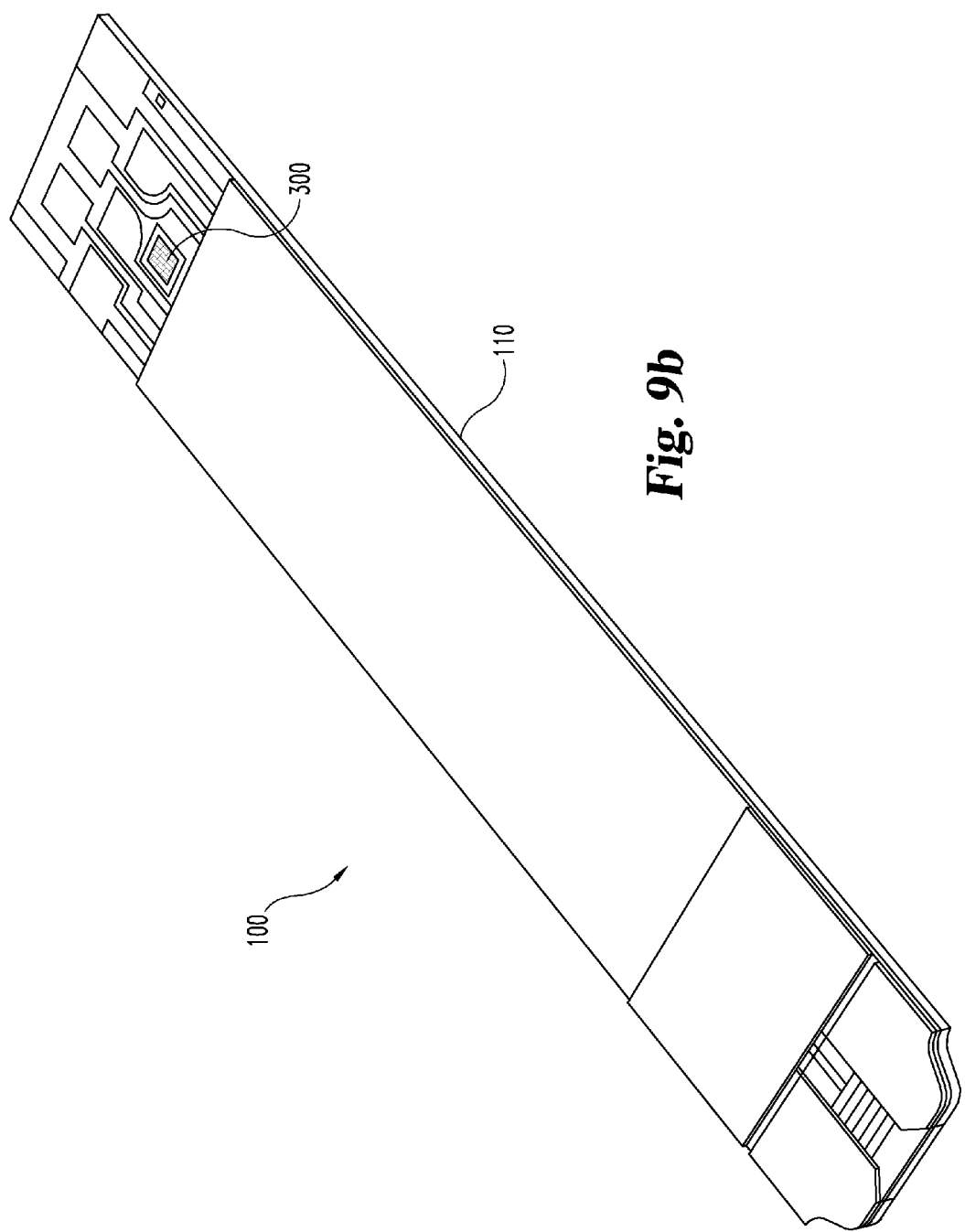

FIGS. 9a, 9b and 9c illustrate additional features of test element 100 which are not depicted in FIG. 8 for clarity of illustration. Such features should be understood as illustrative of one exemplary embodiment, wherein other or differently configured such features may also be employed in the context of the present invention. Reagent layer 220 is provided over a portion of the conductive material on substrate 110. Reagent layer 220 may comprise a number of reagents depending upon the particular analyte(s) to be detected or measured by test element 100. In certain embodiments the reagent layer comprises compositions reactable with a sample to provide indicia relating to blood glucose. In certain embodiments the reagent layer 220 comprises compositions reactable with a sample to provide indicia of cholesterols, triglycerides, lipids and/or other analytes associated with cardiovascular health. In certain embodiments the reagent layer 220 comprises compositions reactable with a sample to provide indicia of carbohydrates, amino acids, antibodies, proteins, nucleic acids, peptides, viruses, bacteria, markers, drugs, toxins, and other biological analytes which can be measured to identify a number of diseases, disorders and conditions. In other embodiments the reagent layer 220 comprises compositions reactable with a sample to provide indicia of analytes such as pollutants, toxins or contaminants. Table 1 below lists a number of non-limiting examples of analyte-enzyme-mediator combinations according to various exemplary reagent layers.

TABLE 1

| Analyte | Enzymes | Mediator (Oxidized Form) | Additional Mediator |
|---|---|---|---|
| Glucose | Glucose Dehydrogenase and Diaphorase | Ferricyanide | N/A |
| Glucose | Glucose Oxidase | Ferricyanide | Oxygen |
| Glucose | Glucose Dehydrogenase | Quinonediimine | N/A |
| Glucose | Glucose-Dehydrogenase (Quinoprotein) | Ferricyanide | N/A |
| Glucose | Glucose Dehydrogenase Flavin Adenine Dinucleotide (GDH-FAD) | Ferricyanide | N/A |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or |

TABLE 1-continued

| Analyte | Enzymes | Mediator (Oxidized Form) | Additional Mediator |
|---|---|---|---|
| Triglyecrides | Lipoprotein Lipase, Glycerol Kinase, and Glycerol-3-Phosphate Oxidase | Ferricyanide or Phenazine Ethosulfate | Phenazine Ethosulfate Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | N/A |
| Lactate Dehydrogenase | Diaphorase | Ferricyanide | Phenazine Ethosulfate, or Phenazine Methosulfate |
| Pyruvate | Pyruvate Oxidase | Ferricyanide | N/A |
| Alcohol | Alcohol Oxidase | Phenylene diamine | N/A |
| Bilirubin | Bilirubin Oxidase | 1-Methoxy-Phenazine Methosulfate | N/A |
| Uric Acid | Uricase | Ferricyanide | N/A |

FIG. 9a further illustrates adhesive 230 and spacer 240 which are provided over the reagent layer 220, a portion of substrate 110 and a portion of the conductive material on substrate 110. Adhesive 230 and spacer 240 extend from the proximal end of substrate 110 to line 211. The portion of the substrate to distal to line 211 including the test element contact pads and coding feature 300 is not covered by adhesive 230 and spacer 240. Adhesive 230 and spacer 240 include voids 232 and 242, respectively, which define in part a sample chamber of test element 100. The sample chamber of test element is operable to receive a sample which is to be tested and to contact the sample with the reagent layer 220 in a region which operatively contacts the working electrode 121, the counter electrodes 120 and 122, and sample detect electrodes 131 and 132. Adhesive 250, which includes void 252, and cover members 260,260' are provided over a portion of spacer 240 and also define the sample chamber in part. The embodiment illustrated in FIGS. 9a, 9b and 9c depicts a sample chamber configured to receive a sample on the side of test element 100. Additional embodiments include sample chambers configured to receive samples from an end, top surface or bottom surface of test element 100.

It shall be understood that a number of further embodiments include additional and alternate test element attributes and features in addition to or instead of those illustrated in FIGS. 8, 9a, 9b and 9c. For example, additional details regarding exemplary test elements configured for use with electrochemical measurement techniques are disclosed in U.S. Pat. No. 7,727,467 which describes the ACCU-CHEK® Aviva test strip and is hereby incorporated herein by reference in its entirety as an additional non-limiting example. Furthermore, additional details of test element configured for use with optical measurement techniques are disclosed in U.S. Pat. No. 7,008,799 which describes the ACCU-CHEK® Compact test strip and which is hereby incorporated herein by reference in its entirety as an additional non-limiting example. Furthermore, as illustrated in FIGS. 8, 9a, 9b and 9c test element 100 is in the form of a single use, disposable electrochemical test strip having a substantially rectangular shape. It shall be appreciated that further embodiments include test element of a number of different forms including, for example, test strips of different configurations, dimensions or shapes, non-strip test elements, disposable test elements, reusable test elements, colorimetric test elements, micro-arrays, lab-on-chip devices, bio-chips, bio-discs, bio-cds or other test elements. It shall be further appreciated that exemplary coding features according to the present disclosure may be advantageously applied to these and other analyte test elements.

Figure 10A:
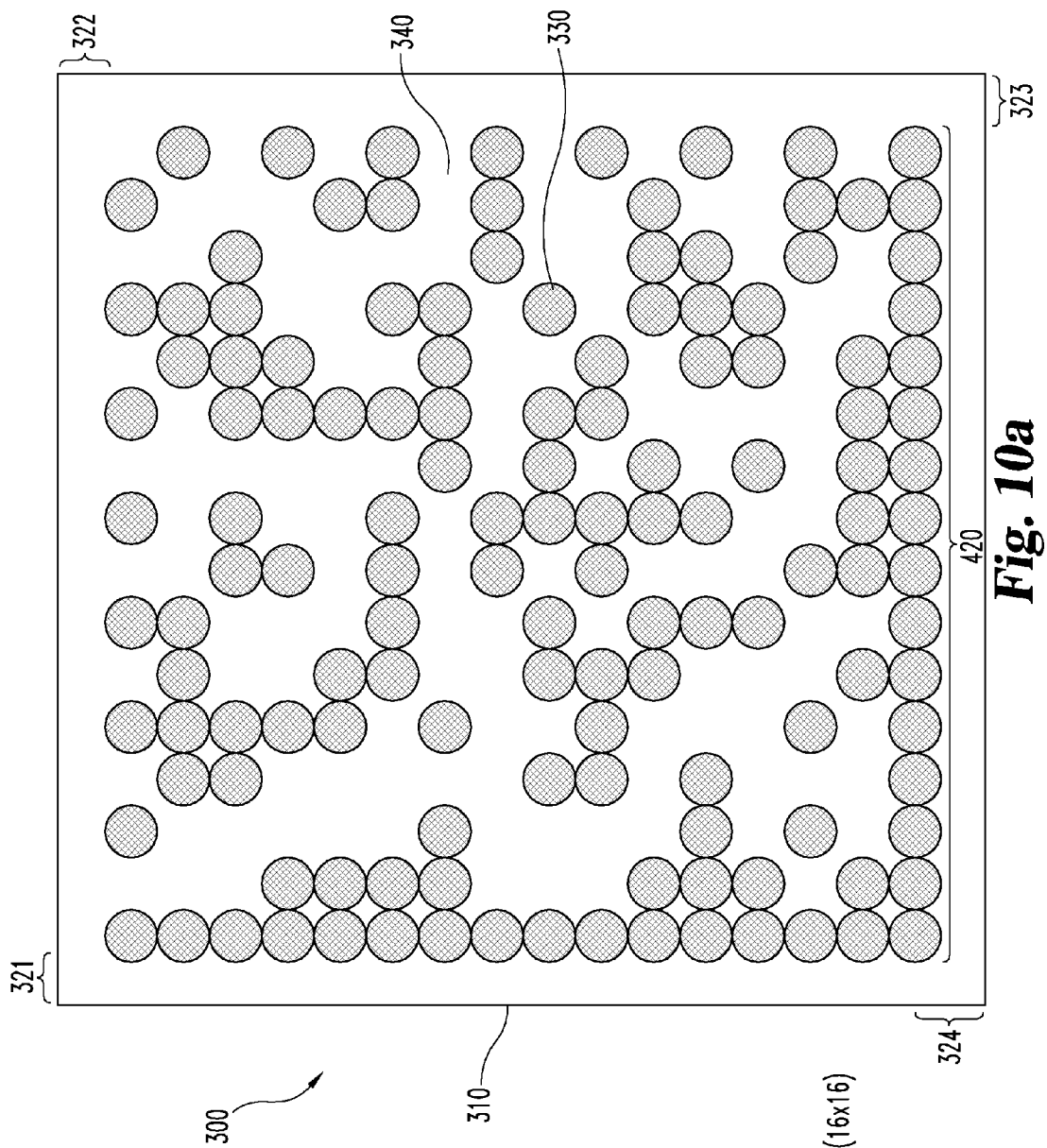
FIGS. 10a and 10b are top views of exemplary coding features for a test element, showing 16×16 and 14×14 pattern dimensions, respectively.
Figure 10B:
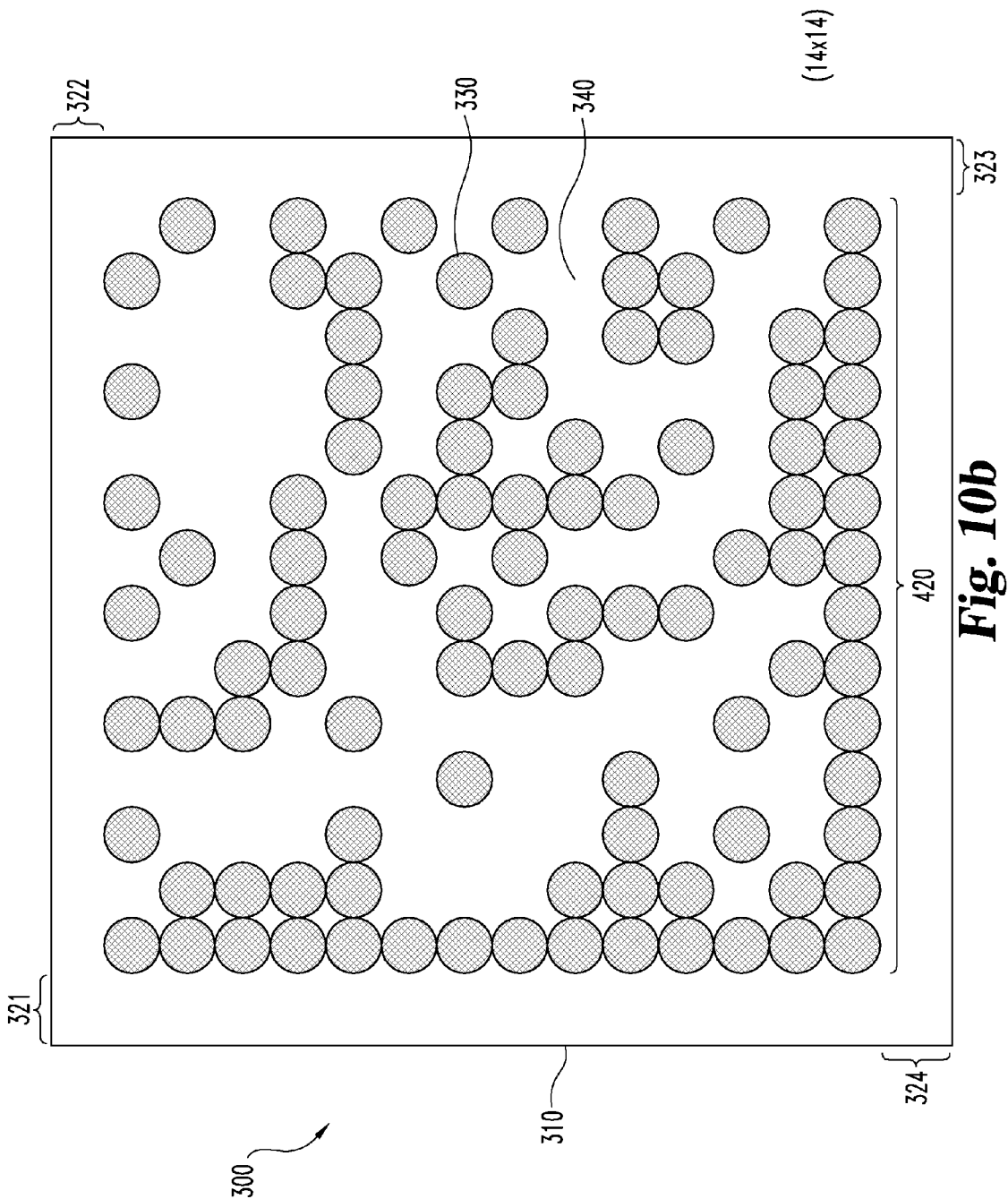

FIGS. 10a and 10b illustrate embodiments of a coding feature 300 of test element 100 in further detail. As shown in FIG. 10a, coding feature 300 encodes information in two dimensions through a pattern of conductive material 310 which is provided on substrate 110 of test element 100. The two-dimensional pattern of FIG. 10a is defined within a 16×16 matrix area 320 defining readable regions indicated with dashed lines. In each readable region of the matrix area 320 the conductive material is either left intact (for example, as illustrated in region 340) or ablated (for example, as illustrated in region 330). The pattern of intact and ablated regions within matrix area 320 can be optically read and decoded using an optical reader and associated processing circuitry and algorithms.

Coding feature 300 provides an information density of 96 bits per square millimeter or greater. As illustrated in FIG. 10a, conductive material is a substantially 1 mm×1 mm square with a 0.1 mm border (indicated with braces 321, 322, 323 and 324) surrounding matrix area 320. The perimeter readable regions of matrix area 320 serve as alignment/orientation bits with each readable region of the lower perimeter and the left perimeter being ablated, and the upper perimeter and the right perimeter being ablated at every-other readable region. The remaining interior 14×14 sub-matrix of readable regions typically includes 96 data bits and 96 error checking bits which can be encoded, for example, using ECC200 error checking and correction standards to permit the information from the remaining interior 14×14 sub-matrix to be read and recovered even with up to 30% damage of the readable regions therein. Matrix area 320 may be based on a number of coding systems, such as two-dimensional Data Matrix ECC200 code. Other examples of layouts for matrix area 320 include Micro QR, QR, and Aztec. The information from the coding feature 300 can also be encrypted. Thus, a preferred information density of 96 bits per square millimeter is provided in combination with 30% damage resistance and encryption. It shall be understood that an increase in the information density may be achieved by reallocating a number of error checking bits as data bits. Reallocating error checking bits as data bits will have increased the information density provided with a corresponding decrease in the degree of pattern damage detection and correction that can exist while still allowing for at least some information recovery. Conversely reallocating data bits as error checking bits will decrease information density, but increase the degree of damage that can occur while still allowing information recovery. FIG. 10b shows an embodiment in which the matrix area 320 is 14×14. A similar description as set forth above with regard to FIG. 10a adjusted to the smaller scale of FIG. 10b will be understood by those of ordinary skill in the art of data matrix codes.

In one embodiment, the two-dimensional pattern of coding feature 300 is formed using a galvo-driven UV laser to ablate positions in a gold mask feature provided on the surface of an electrochemical test element. An exemplary laser system is a series 3500 diode pumped ND-YVO4 laser available from DPSS Lasers Inc. having a 1 micrometer base wavelength frequency tripled by a harmonic generation unit to provide a 355 nanometer wavelength output. The position of the output beam is controlled by galvo-driven mirrors. Output spot size can be varied from 10 micrometers to 25 micrometers. Average power output is 1 W with peak power output of 1.5 kW. Pulse frequency is 30 kHz and pulse length is 30 nanoseconds. Pulse energy is 33 micro Joules and pulse stability is +/−5% or less. Other exemplary laser system include excimer laser systems, laser systems utilizing masks and scribing laser systems.

Ablation to form coding feature 300 can also efficiently occur at the time the conductive pattern of, e.g., electrodes on the substrate is formed by ablation. Similarly, if such conductive pattern is printed or inkjetted, efficiency is achieved by using a common technique for also forming coding feature 300. Alternatively, because practicalities of manufacturing a test element with coding relating to, e.g., calibration information would generally require substantially complete manufacture and testing of lots or batches of test elements in order to determine such calibration information, ablation (or printing or inkjetting) of the coding feature in other embodiments occurs after the conductive pattern is formed and manufacture of the remaining features of the test element is at least substantially completed. Thus, an area of the material is provided at the location for the coding feature 320 (or such area is left blank to receive a printed or inkjetted coding feature).

The two-dimensional pattern of coding feature 300 can also be formed using other equipment and techniques, for example, in certain embodiments a multi-laser micro array is used to create the two-dimensional code pattern. This micro array can be either two-dimensional and create the code pattern in one pulse by controlling which laser array element is enabled, or the array can be one-dimensional and create the code pattern as the material passes under the laser. Furthermore, while the material of coding feature 300 in some embodiments described herein comprises gold or an alloy thereof, additional or alternate materials may be used including the conductive material alternatives described above in connection with FIG. 8, nonconductive materials, other nanocoated metals, printed inks, or thermochromic coatings/materials or other materials effective to permit the formation of optically contrasting patterns between the material of the coding feature and the underlying structure.

In some embodiments exemplary embodiments, a coding feature 300 may be formed directly in a single material by laser ablating or selected portions of the material, or otherwise removing or altering the material to provide an optically contrasting pattern. In certain embodiments a two-dimensional code is marked on a surface of a PET component of a test element using a galvo-driven UV laser. In one form the top surface of the substrate is marked. Depending on laser transmittance through the substrate chosen, the contrasting mark can be made by passing the laser through the substrate onto the surface being structured or directly onto the surface being structured. In another form the bottom surface of the substrate is marked. In a further form a cover or spacer feature is marked. In certain additional embodiments a two-dimensional code is marked on an acrylic hardcoat applied to the top or bottom surface of a substrate. In certain further embodiments a two-dimensional code is marked on an ink region printed on the top or bottom surface of the substrate or on another location of a test element.

Figure 11A:
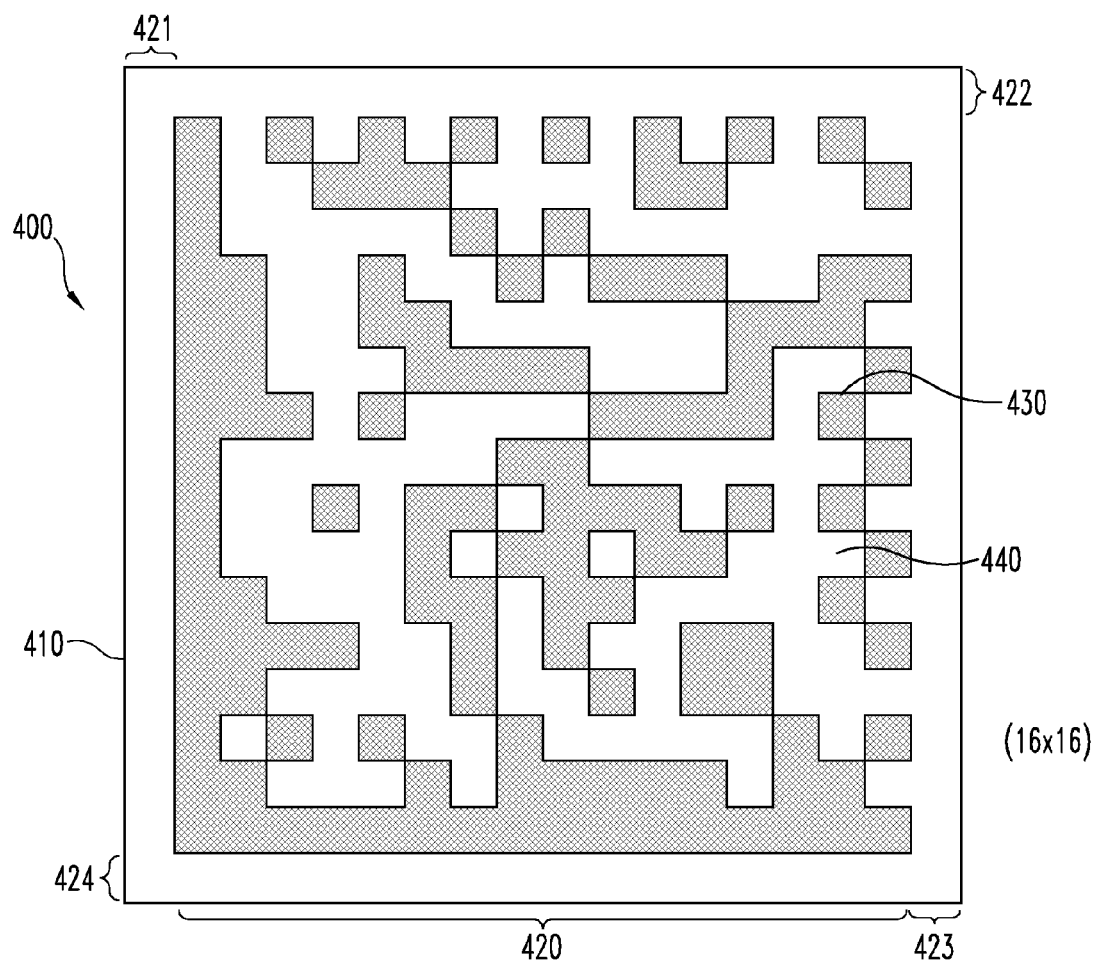
FIGS. 11a and 11b are top views of other exemplary coding features for a test element, showing 16×16 and 14×14 pattern dimensions, respectively.
Figure 11B:
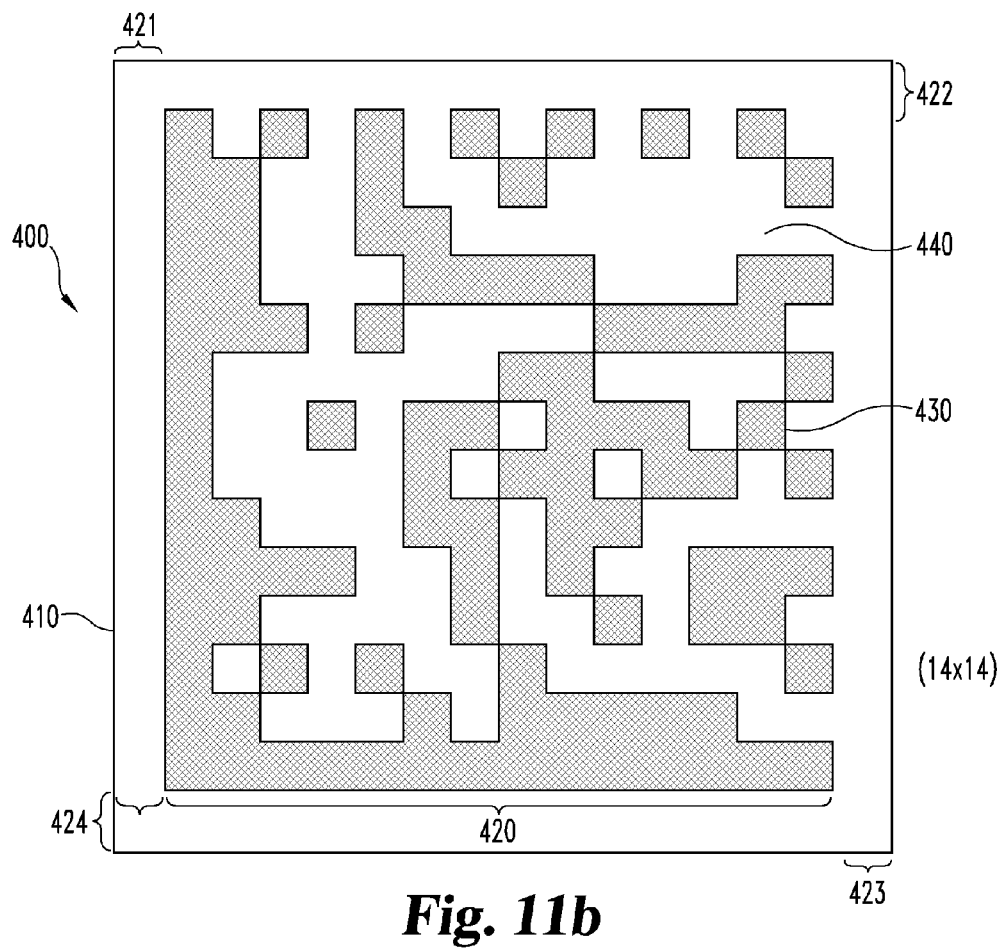

FIGS. 11a and 11b illustrate additional exemplary embodiments of a coding feature 400 including conductive material 410, borders 421, 422, 423 and 424, intact regions such as region 440 and ablated regions such as region 440. In FIG. 11b, for example, coding feature 400 provides information density of 64 data bits per square millimeter with 30% damage resistance is provided through an overall 14×14 matrix (FIG. 11a by contrast has an overall 16×16 matrix) having an orientation perimeter and an interior 12×12 matrix including 64 data bits and 80 error checking bits. As illustrated in FIG. 11b the ablated regions are substantially square in shape as opposed to the generally circular ablated spot regions illustrated in FIGS. 10a and 10b. These are but two alternatives for providing an optically readable pattern, and a number of other constituent pattern shapes may be employed. The constituent shapes of the pattern may be dictated by the properties of the equipment used to encode information on the pattern. Furthermore, the additional and alternate attributes and features of coding feature 300 described above in connection with FIGS. 10a and 10b are also applicable to FIGS. 11a and 11b.

The encoded/transferred information of coding features 300 and 400 as well as that of additional exemplary coding features may include information relating to the test elements which bear the coding features including, for example, product performance, electrochemical test element attribute, error checking information expiration date, product ID (countries or regions of approved or designated sale or use), slopes and intercepts of blood and control solutions, strip-lot ID, and many other features. Further details of the information encoded in two exemplary two-dimensional patterns are summarized below.

ENCODED INFORMATION EXAMPLE 1

Encoded Information Example 1 includes a 14×14 two-dimensional data matrix ECC200 open source definition code having 64 data bits, 80 error checking bits, and 52 perimeter alignment/orientation bits. Other bit usage distributions are possible (including using all 144 bits for data), but will require development of new algorithms. In this example, the known open source algorithms are used for each of illustration and instruction. In an exemplary use of a code feature such as described herein, the data bits could be encoded to convey the following information:
  Blood Slope—16 bits
  Blood Intercept—16 bits
  Lot ID—10 bits
  Expiration Date—8 bits
  Product ID—8 bits
  Product type—2 bits
  Meter Features—4 bits.

ENCODED INFORMATION EXAMPLE 2

Encoded Information Example 2 includes a 16×16 two-dimensional data matrix ECC200 open source definition code having 96 data bits, 96 error checking bits, 60 perimeter alignment/orientation bits, and 4 free bits. As noted in Example 1, other bit usage distributions are possible and are within the skill of a person of ordinary skill in the art. In an exemplary use of a 16×16 code feature, the data bits could be encoded to convey the information encoded by the data bits as set forth in Example 1, with the following additional information:
  Controls Slope—16 bits
  Controls Intercept—16 bits The information encoded by coding the exemplary coding features described herein may be transferred to a meter in order to perform calibration, error checking, expiration, checking, product type checking, strip type checking, use authorization checking and other functionalities, for example, expiration date information may also be used to modify the strip performance algorithm. Such a volume of information and types of information are useful for maintaining a highly accurate system throughout an electrochemical test element's shelf life.

Figure 12:
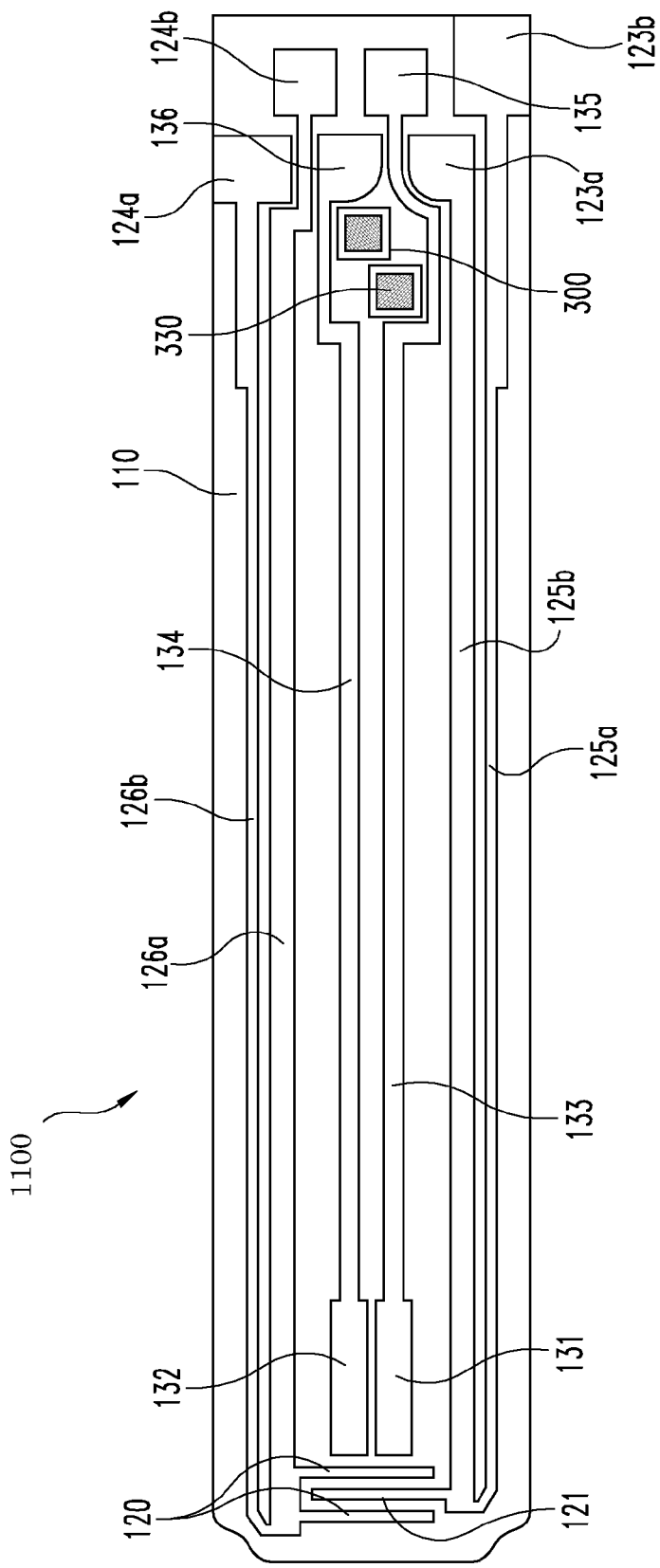
FIG. 12 is a top view of a portion of an exemplary test element.

FIG. 12 illustrates an exemplary test element 1100 including the features of test element 100 described above in connection with FIG. 8 and which are denoted with identical reference numerals. Test element 1100 further includes coding feature 330. Coding feature may be provided in any of the manners and using any of the techniques as described above with respect to coding feature 300 and may include the same or similar physical and compositional features and attributes as coding feature 300. In an exemplary embodiment coding feature 330 encodes information uniquely identifying test element 1100. The uniquely identifying information may comprise a number of forms including a serial number, a lot number in combination with a serial number, a year or date, for example a "born on" date, in combination with a lot number and/or a serial number, other uniquely identifying information, and/or combinations of the foregoing.

As illustrated in FIG. 12 coding feature is positioned on an upper surface of the substrate 110 proximate coding feature 300. In the illustrated position, coding feature 330 is readable once it is created during manufacture of the test element 1100 and remains readable after the manufacture of the test element 1100 is completed. In further embodiments coding feature 330 may be provided in a number of additional or alternate locations on test element 1100. In further embodiments, coding feature 330 may be provided in other positions, for example, in other locations on the upper surface of the substrate 110, on the lower surface of substrate 110, or on another structure of test element 1100 such as cover such as a spacer or cover member. In certain embodiments coding feature is positioned to be readable during a portion of the manufacture of test element 1100, but covered after a certain point during manufacturing, for example, by one or more adhesive, spacer, or cover members or combinations thereof.

Coding feature 330 may be utilized to uniquely identify test element 1100 at multiple points during the life cycle of test element 1100, including manufacturing, product testing and quality control operations, during measurement involving test element 1100, and at points after measurement involving test element 1100. Coding feature 330 may be used in sheet based manufacturing processes as well as reel to reel manufacturing processes. In certain embodiments coding features such as coding feature 330 are provided to uniquely identify each test element in a batch a test element. Reagent compositions which may include one or more mediators are subsequently applied to each of the test elements. The characteristic of the reagent compositions may vary within the batch of test elements necessitating different calibrations for measurement equipment used in connection with different test strips of the batch. Calibration data accounting for the variation in the characteristics of the reagent compositions are determined and associated with the unique identification information previously provided for each o the test elements or with ranges of uniquely identifying information. An additional coding feature which encodes the calibration information particular to each test strip, for example coding feature 300, is then applied to each test strip. The uniquely identifying information of the previously applied coding features are used to determine the particular calibration information that should be applied to each test element.

Figure 13:
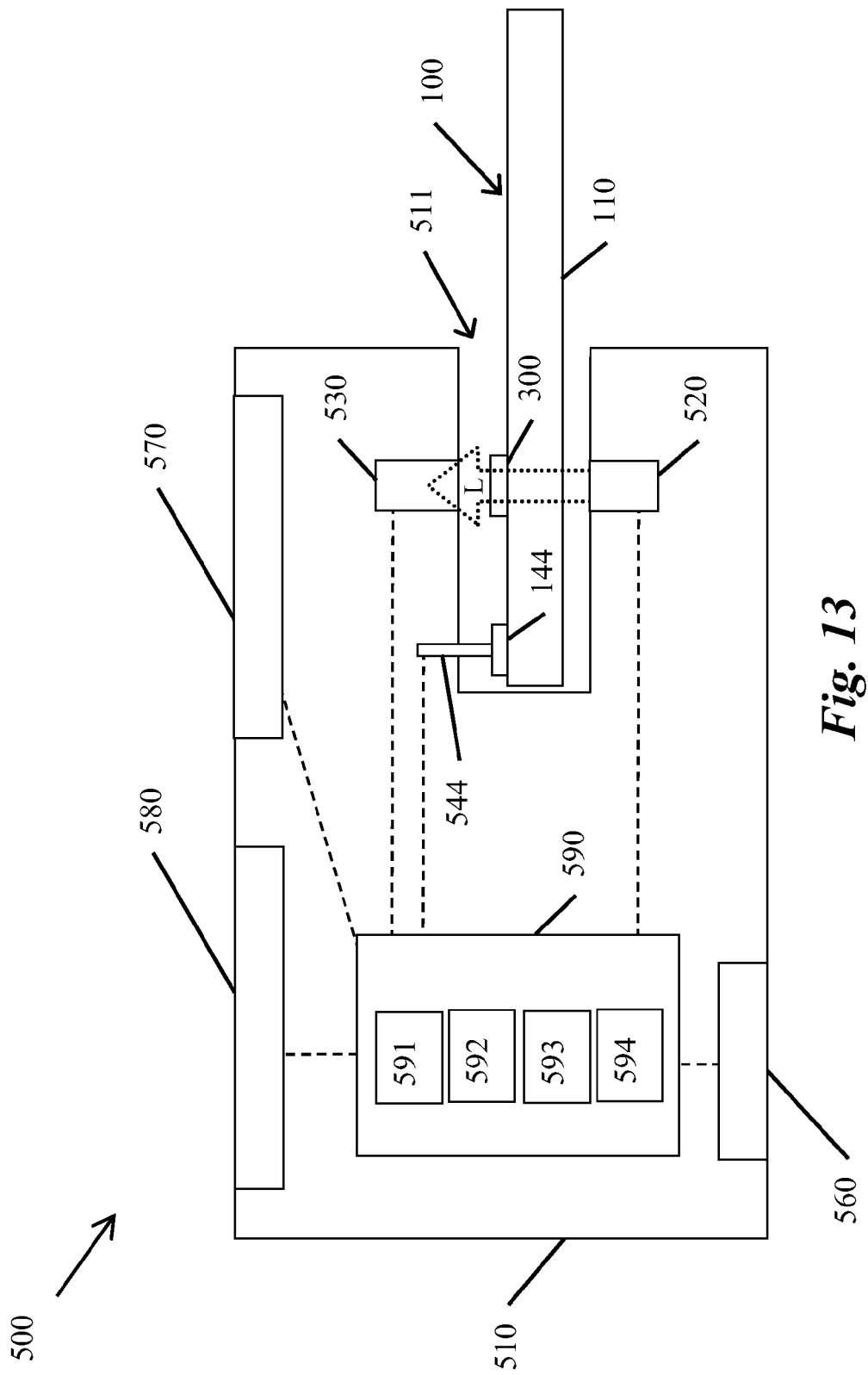
FIG. 13 is a schematic diagram of an exemplary testing system including a meter and a test element.

FIG. 13 illustrates an exemplary testing system 500 including a meter 510 and test element 100. Meter 510 includes meter circuitry 590 which is connected to a display 580, a user input interface 570, a communications interface 560, a plurality of electrical contacts 544, an optical source 520, and an optical sensor 530. Meter circuitry 590 has a number of subsystems including power source (such as a battery, not shown) and circuitry 591, microprocessor circuitry 592, memory circuitry 593, and signal processing circuitry 594 which are interoperable with the other components of meter 510 to provide power, transmit information, receive information, and process, store and display information including the results of analyte testing operations performed by testing system 500. Meter 510 may also include additional or alternate components, features and functionalities including, for example, those described in U.S. Pat. Nos. 5,352,351; 4,999,482; 5,438,271; 6,645,368; 5,997,817; 6,662,439; RE 36,268; 5,463,467; 5,424,035; 6,055,060; 6,906,802; and 5,889,585; the disclosures of which are hereby incorporated herein by reference in their entireties as non-limiting examples.

As illustrated in FIG. 13, test element 100 and meter 510 are in an operatively coupled configuration. Test element 100 is received in a receptacle 511 of meter 510. A plurality of electrical contacts 544 of meter 510 are electrically coupled to a corresponding plurality of electrical contact pads 144 of test element 100. In embodiments where the test element 100 is as illustrated and described above in connection with FIGS. 8, 9a, 9b and 9c, working electrode contact pads 123a and 123b, counter electrode contact pads 124a and 124b, and contact pads 135 and 136 are each electrically coupled with a corresponding electrical contact of the meter 510. In this configuration meter 510 is operable to provide power to, transmit information to, and receive information from test element 100 in order to perform an analyte testing operation.

In the coupled configuration illustrated in FIG. 13, information from coding feature 300 of test element 100 may be transferred to meter 510. In certain embodiments information transfer from coding feature 300 to meter 510 occurs before an analyte testing operation is performed, however, certain other embodiments contemplate simultaneous information transfer and testing, temporally overlapping information transfer and testing, alternating or iterative information transfer and testing, post-testing information transfer, or other operational orders. The transferred information may include the information described above in connection with FIGS. 3 and 4 as well as additional or alternate information.

In an exemplary information transfer operation between coding feature 300 of test element 100 and meter 510, meter circuitry 590 signals optical source 520 to provide an optical output indicated by dashed arrow L. The optical output L encounters substrate 110 of test element 100 which has optical transmittance characteristics effective to transmit optical output L (or a measurably significant portion thereof) through substrate 110. Optical output L (or the transmitted portion thereof) next encounters coding feature 300. Coding feature 300 encodes information in a two-dimensional pattern in which a first set of pattern regions has a first set of optical transmittance characteristics relative to optical output L and a second set of pattern regions has a second set of optical transmittance characteristics relative to optical output L. When optical output L encounters coding feature 300, the information encoded by the two-dimensional pattern of coding feature 300 is modulated onto optical output L by the first and second transmittance characteristics of the pattern of coding feature 300. The modulated optical output then proceeds to optical sensor 530 which detects the modulated optical output and provides a corresponding electrical output that includes the information from coding feature 300 to meter circuitry 590 which, in turn, receives, processes, stores the information and makes use of it in connection with analyte testing operations.

As illustrated in FIG. 13 optical sensor 520 is located on the same side of test element 100 as coding feature 300 such that optical output first passes through substrate 110 of test element 100 and then encounters coding feature 300. This configuration minimizes the influence of scatter effects attributable to the optical characteristics of the substrate 110. In embodiments where the optical output first passes through coding feature 300 and then through substrate 110 of test element 100 the substrate may be selected to minimize the influence of scatter effects. Additional sensor components, for example, a collimator lens and/or optical sensors of increased resolution or sensitivity may be also be utilized to account for the influence of scatter effects.

INFORMATION TRANSFER EXAMPLE 1

In a first exemplary information transfer system the optical source is an infrared light emitting diode ("LED"), and the sensor is a CMOS sensor with 656×496 resolution and 2.8 micrometer pixel size. A suitably sized CCD sensor may also be used for the sensor. The LED is preferably a red wavelength LED and may also be an infrared, near infrared, red, white, green, yellow or other wavelength LED. A double convex lens is used to provide 1× magnification with the lens diameter selected to be substantially equal to the focal length, for example lens diameters and focal lengths of 1.2 mm, 1.8 mm, 2 mm and 3 mm.

INFORMATION TRANSFER EXAMPLE 2

In a second exemplary information transfer system the optical source is an LED, the sensor is a CMOS sensor with 725×480 resolution and 6.0 micrometer pixel size. The LED is preferably a red wavelength LED and may also be an infrared, near infrared, red, white, green, yellow or other wavelength LED. In the first example a double convex lens is used to provide 1× magnification with the lens diameter selected to be substantially equal to the focal length, for example lens diameters and focal lengths of 1.2 mm, 1.8 mm, 2 mm and 3 mm.

INFORMATION TRANSFER EXAMPLE 3

In a third exemplary information transfer system the optical source is an collimated light source, the sensor is a CMOS sensor with 725×480 resolution and 6.0 micrometer pixel size. The collimated light source is preferably a red wavelength LED and may also be an infrared, near infrared, red, white, green, yellow or other wavelength LED.

Figure 14A:
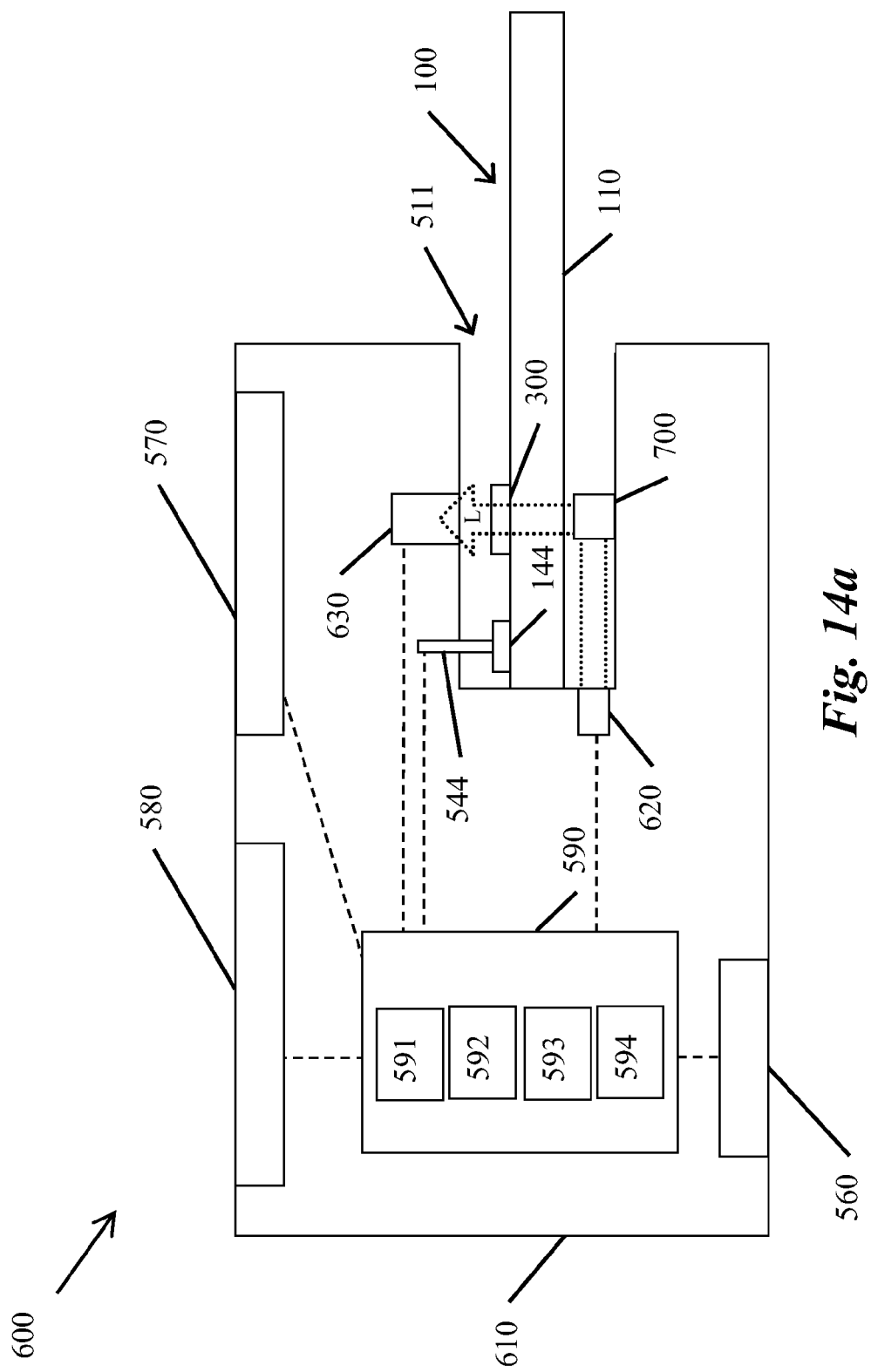
FIGS. 14a, 14b and 14c are schematic diagrams of additional exemplary testing system including a meter and a test element.

FIG. 14a illustrates an exemplary testing system 600 including a meter 610 and test element 100. Meter 610 includes a number of the same features as meter 510 described above in connection with FIG. 13 and labeled with the same references numerals as the corresponding features of FIG. 13. Meter 610 further includes light source 620 and detector 630. Light source 620 is configured to direct an optical output to optical system 700 which may comprise one or more lenses, one or more mirrors, one or more prisms or combinations thereof. Optical system 700 directs the optical output to substrate 110 of test element 100 which has optical transmittance characteristics effective to transmit the optical output (or a measurably significant portion thereof) through substrate 110 as indicated by dashed arrow L. The optical output (or the transmitted portion thereof) next encounters coding feature 300. Coding feature 300 encodes information in a two-dimensional pattern in which a first set of pattern regions has a first set of optical transmittance characteristics relative to the optical output and a second set of pattern regions has a second set of optical transmittance characteristics relative to optical output. When optical output encounters coding feature 300, the information encoded by the two-dimensional pattern of coding feature 300 is modulated onto optical output by the first and second transmittance characteristics of the pattern of coding feature 300. The modulated optical output then proceeds to optical sensor 630 which detects the modulated optical output and provides a corresponding electrical output that includes the information from coding feature 300 to meter circuitry 590 which, in turn, receives, processes, stores the information and makes use of it in connection with analyte testing operations.

Figure 14B:
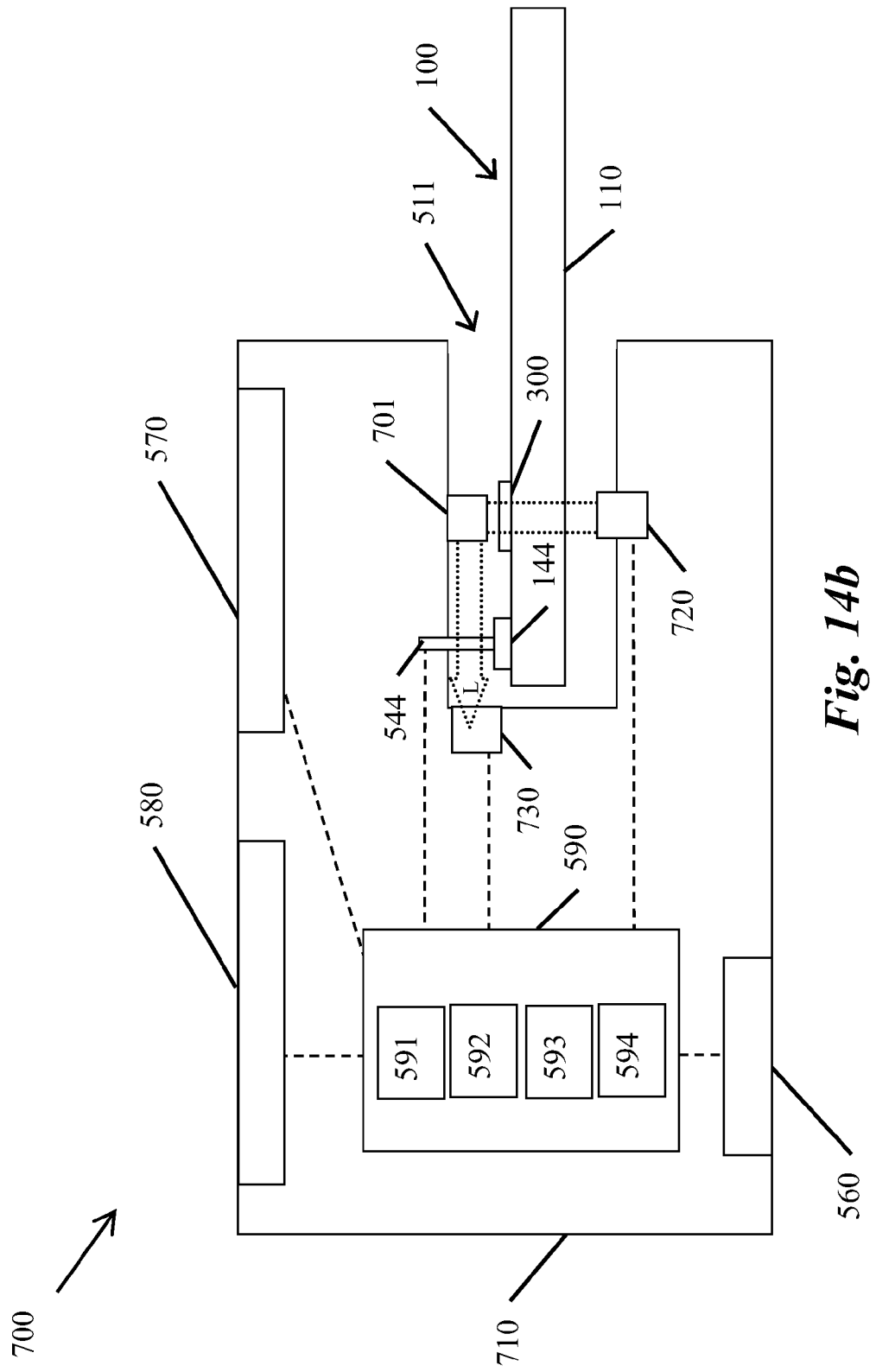

FIG. 14b illustrates an exemplary testing system 700 including a meter 710 and test element 100. Meter 710 includes a number of the same features as meter 510 described above in connection with FIG. 13 and labeled with the same references numerals as the corresponding features of FIG. 13. Meter 710 further includes light source 720 and detector 730. Light source 720 is configured to direct an optical output to substrate 110 of test element 100 which has optical transmittance characteristics effective to transmit the optical output (or a measurably significant portion thereof) through substrate 110. The optical output (or the transmitted portion thereof) next encounters coding feature 300. Coding feature 300 encodes information in a two-dimensional pattern in which a first set of pattern regions has a first set of optical transmittance characteristics relative to the optical output and a second set of pattern regions has a second set of optical transmittance characteristics relative to optical output. When optical output encounters coding feature 300, the information encoded by the two-dimensional pattern of coding feature 300 is modulated onto optical output by the first and second transmittance characteristics of the pattern of coding feature 300. The modulated optical output then proceeds to optical system 701 which may comprise one or more lenses, one or more mirrors, one or more prisms or combinations thereof. Optical system 701 directs the optical output to optical sensor 730 which detects the modulated optical output and provides a corresponding electrical output that includes the information from coding feature 300 to meter circuitry 590 which, in turn, receives, processes, stores the information and makes use of it in connection with analyte testing operations. Optical system 701 and detector 730 are positioned and configured so that the optical output transmitted between them is not blocked or interfered with by electrical contacts 544 or electrical contact pads 144 of test element 100. This may be accomplished, for example, by configuring optical system 701 to direct optical output to the side of or around electrical contacts 544 and electrical contact pads 144 of test element 100 and configuring detector 730 in a corresponding receiving position. In additional embodiments, this may be accomplished by configuring optical system 701 to direct optical output between one or more electrical contacts 544 and configuring detector 730 in a corresponding receiving position.

Figure 14C:
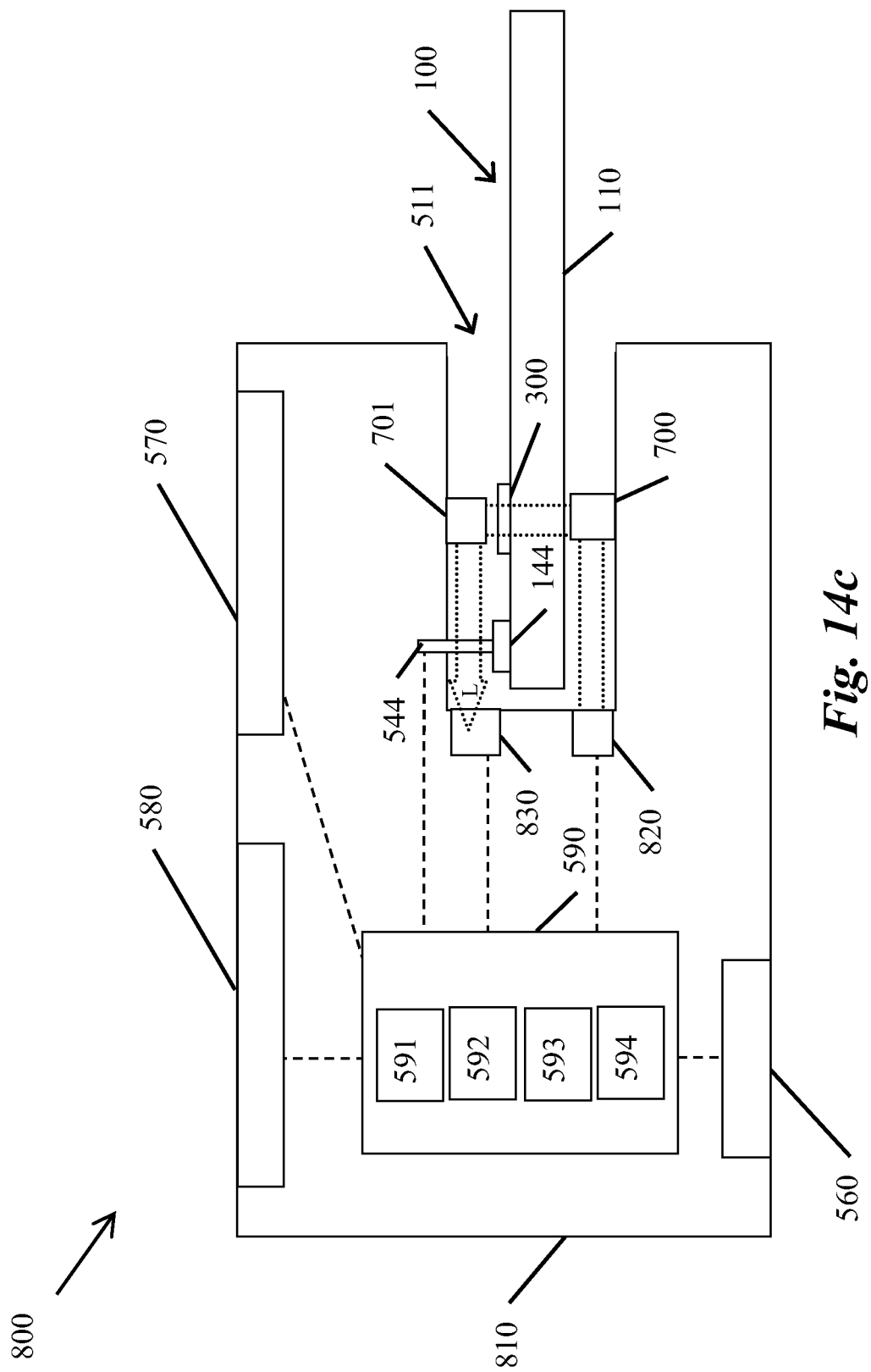

FIG. 14c illustrates an exemplary testing system 800 including a meter 810 and test element 100. Meter 810 includes a number of the same features as meter 510 described above in connection with FIG. 13 and labeled with the same references numerals as the corresponding features of FIG. 13. Meter 810 further includes light source 820 and detector 830. Light source 820 is configured to direct an optical output to optical system 700 which may comprise one or more lenses, one or more mirrors, one or more prisms or combinations thereof. Optical system 700 directs the optical output to substrate 110 of test element 100 which has optical transmittance characteristics effective to transmit the optical output (or a measurably significant portion thereof) through substrate 110. The optical output (or the transmitted portion thereof) next encounters coding feature 300. Coding feature 300 encodes information in a two-dimensional pattern in which a first set of pattern regions has a first set of optical transmittance characteristics relative to the optical output and a second set of pattern regions has a second set of optical transmittance characteristics relative to optical output. When optical output encounters coding feature 300, the information encoded by the two-dimensional pattern of coding feature 300 is modulated onto optical output by the first and second transmittance characteristics of the pattern of coding feature 300. The modulated optical output then proceeds to optical system 701 which may comprise one or more lenses, one or more mirrors, one or more prisms or combinations thereof. Optical system 701 directs the optical output to optical sensor 730 which detects the modulated optical output and provides a corresponding electrical output that includes the information from coding feature 300 to meter circuitry 590 which, in turn, receives, processes, stores the information and makes use of it in connection with analyte testing operations. Optical system 701 and detector 830 are positioned and configured so that the optical output transmitted between them is not blocked or interfered with by electrical contacts 544 or electrical contact pads 144 of test element 100. This may be accomplished, for example, by configuring optical system 701 to direct optical output to the side of or around electrical contacts 544 and electrical contact pads 144 of test element 100 and configuring detector 830 in a corresponding receiving position. In additional embodiments, this may be accomplished by configuring optical system 701 to direct optical output between one or more electrical contacts 544 and configuring detector 830 in a corresponding receiving position.

The exemplary embodiments of the invention summarized above and illustrated and described in detail in the figures and foregoing description are illustrative and not limiting or restrictive. Only the presently preferred exemplary embodiments have been shown and described and all changes and modifications that come within the scope of the invention are to be protected. It should be understood that various features and aspects of the embodiments described above may not be necessary and embodiments lacking the same are also protected.

What is claimed is:

1. An apparatus comprising: a test element operable to receive a sample and to provide an indication of an analyte of the sample to a meter, the test element comprising a substrate and an optically readable pattern provided on the substrate and encoding information relating to the test element, the substrate having an optical transmittance relative to a light source, the optically readable pattern comprising one or more opaque marked portions and one or more unmarked portions, the optically readable pattern being readable under stationary transillumination by the light source as a shadow image projected onto a sensor;
wherein the test element comprises a second optically readable pattern configured to encode different information relating to the test element than the information encoded by said optically readable pattern, and the second optically readable pattern is readable under transillumination by the light source during a portion of the manufacturing of the test element, and unreadable under transillumination by the light source at the completion of manufacturing.

2. The apparatus according to claim 1 wherein a transillumination optical pathway through the test element is defined by and consists essentially of the substrate and the optically readable pattern.

3. The apparatus according to claim 1 wherein the test element comprises a sample chamber, a reagent, a working electrode, and a counter electrode, and the test element is operable to receive a sample in the sample chamber, react the sample with the reagent, and provide an indication of an analyte of the sample when the working electrode and the counter electrode are electrically coupled with the meter.

4. The apparatus according to claim 1 wherein the optically readable pattern comprises an information density of about 64 bits per square millimeter or greater.

5. The apparatus according to claim 1 wherein the optically readable pattern comprises a conductive material disposed on a surface of the substrate and defining one or more void regions exposing the substrate.

6. The apparatus according to claim 1 wherein the information relating to the test element includes calibration information relating to a reagent.

7. The apparatus according to claim 1 wherein the information relating to the test element includes slope information, intercept information, lot information, and expiration information.

8. The apparatus according to claim 1 further comprising the meter, the light source, and the sensor.

9. The apparatus according to claim 8 wherein the meter is configured to receive the test element, the light source is configured to illuminate a portion of a first surface of the test element received by the meter, and the sensor configured to detect light transmitted through the test element.

10. The apparatus of claim 9 wherein the light source faces a first side of the test element when the test element is received by the meter and the detector faces a second side of the test element opposite the first side when the test element is received by the meter.

11. The apparatus according to claim 1 wherein the information encoded by the optically readable pattern remains recoverable when up to about 30% of the pattern is damaged.

12. The apparatus according to claim 1 wherein a transillumination optical pathway through the test element consists of the substrate and the optically readable pattern.

13. The apparatus according to claim 12 wherein the substrate consists of a single piece.

14. The apparatus according to claim 1 wherein the test element includes a sample receptacle configured to receive the sample and the optically readable pattern is positioned at a location of the substrate spaced apart from the sample receptacle.

15. The apparatus according to claim 1 wherein the second optically readable pattern is configured to encode information uniquely identifying the test element among a set of test elements.

16. The apparatus according to claim 15 wherein the information relating to the test element encoded by said optically readable pattern is based at least in part upon the uniquely identifying information encoded by the second optically readable pattern.

17. A system comprising:
a test element configured to receive a sample and to provide an indication of an analyte of the sample, the test element comprising a transparent or translucent substrate, an opaque pattern provided on the substrate to encode information relating to the test element, an optical pathway through the test element consisting essentially of the substrate and the pattern, a second opaque pattern provided on the substrate to encode second information relating to the test element, and a second optical pathway through the test element consisting essentially of the substrate and the second opaque pattern, wherein the second opaque pattern is readable by directing light through the second optical pathway to a sensor during a portion of the manufacturing of the test element and unreadable by directing light through the second optical pathway to the sensor source at the completion of manufacturing; and a measurement device configured to interface with the test element to receive the indication of the analyte of the sample, the measurement device comprising an optical source configured to provide light to the optical pathway and an optical sensor configured to receive light from the optical pathway.

18. The system according to claim 17 wherein the test element comprises an electrochemical test element.

19. The system according to claim 18 wherein the information relating to the test element includes information of a reagent of the electrochemical test element.

20. The system according to claim 17 wherein the information relating to the test element includes information to calibrate the measurement device to the test element.

21. The system according to claim 17 wherein the pattern has an information density of about 96 bits per square millimeter or greater.

22. The system according to claim 17 wherein the pattern comprises an area less than about one square millimeter.

23. The system according to claim 17 wherein the test element comprises a single use electrochemical test element having a sample chamber, a reagent, and a working electrode, and a counter electrode, and wherein the test element is operable to receive a sample in the sample chamber, react the sample with the reagent, and provide an indication of an analyte of the sample upon the working electrode and the counter electrode being electrically coupled with a meter.

24. The system according to claim 17 wherein a light path between the optical source and the test element is folded.

25. The system according to claim 17 wherein the optical source provides light to the optical pathway at a first surface of the test element and the pattern is provided on a second surface of the test element substantially opposing the first surface.

26. The system according to claim 17 wherein the optical source is positioned on a first side of the test element and the detector is positioned on a second side of the test element.

27. A method comprising:
providing a meter comprising a light source and an optical sensor;
providing a test element comprising a substrate, a matrix pattern provided on the substrate, an optical pathway consisting essentially of the substrate and the matrix pattern, the optical pathway comprising one or more regions having optical transmittance relative to the light source and one or more regions being substantially opaque relative to the light source a second matrix pattern provided on the substrate, and a second optical pathway consisting essentially of the substrate and the second matrix pattern, the second optical pathway comprising one or more second matrix pattern regions having optical transmittance relative to the light source and one or more second matrix pattern regions being substantially opaque relative to the light source;
reading information encoded by the second matrix pattern by directing light through the second optical pathway at an intermediate point during manufacture of the test element, wherein the information encoded by the second matrix pattern to the meter is not transferable to the meter by directing light through the second optical pathway upon completion of manufacture of the test element;
transferring information encoded by the matrix pattern to the meter by directing light from the light source to the optical pathway and detecting light emitted from the optical pathway with the detector; and
testing a sample for an analyte using the test element, the meter, and the transferred information.

28. The method according to claim 27 wherein the testing includes providing a sample to the test element and evaluating an electrical response of the test element based at least in part upon the transferred information.

29. The method according to claim 27 wherein the test element comprises a sample chamber, a reagent, a working electrode, and a counter electrode, a sample is received by the sample chamber prior to the testing, and the meter is coupled with the test element to provide electrical communication between the meter and the working electrode and between the meter and the counter electrode during the testing.

30. The method according to claim 27 wherein the directing light from the light source to the optical pathway includes directing light to a first surface of the test element with an optical system.

31. The method according to claim 27 further comprising providing a second test element comprising a second substrate and a second matrix pattern provided on the second substrate, and substantially repeating the transferring and testing acts using the second test element.

32. The method according to claim 31 wherein a second matrix pattern encodes information to alter meter operation relative to operation with the first test element.

* * * * *